(12) United States Patent
Bunkers et al.

(10) Patent No.: US 7,332,596 B1
(45) Date of Patent: Feb. 19, 2008

(54) ANTIFUNGAL PROTEINS AND METHODS FOR THEIR USE

(75) Inventors: Greg J. Bunkers, Wildwood, MO (US); Jihong Liang, Chesterfield, MO (US); Cindy A. Mittanck, Ballwin, MO (US); Jeffrey W. Seale, Ballwin, MO (US); Yonnie S. Wu, Vacaville, CA (US)

(73) Assignee: Monsanto Technology LLC, St. Louis, MO (US)

( * ) Notice: Subject to any disclaimer, the term of this patent is extended or adjusted under 35 U.S.C. 154(b) by 306 days.

(21) Appl. No.: 10/421,684

(22) Filed: Apr. 23, 2003

Related U.S. Application Data

(62) Division of application No. 09/732,210, filed on Dec. 7, 2000, now Pat. No. 6,573,361.

(60) Provisional application No. 60/169,513, filed on Dec. 7, 1999, provisional application No. 60/169,340, filed on Dec. 7, 1999.

(51) Int. Cl.
*C07H 21/04* (2006.01)
*C12N 5/10* (2006.01)

(52) U.S. Cl. .................. 536/23.7; 435/6; 435/69.1; 435/254.7; 435/252.3; 435/320.1; 530/300; 530/324

(58) Field of Classification Search .............. 536/23.6, 536/23.7; 435/6, 254.7, 69.1, 252.3, 320.1; 530/324, 300
See application file for complete search history.

(56) References Cited

U.S. PATENT DOCUMENTS

| | | | |
|---|---|---|---|
| 5,773,696 | A | 6/1998 | Liang et al. |
| 6,573,361 | B1 * | 6/2003 | Bunkers et al. ............. 530/324 |

OTHER PUBLICATIONS

Sosa et al., Structure of a ribosomal protein gene in *Mucor racemosus*, Nucleic Acids Research *17*:9319-9331 (1989).

* cited by examiner

*Primary Examiner*—Chih-Min Kam
(74) *Attorney, Agent, or Firm*—Timothy K. Ball, Esq.

(57) ABSTRACT

A novel protein was isolated from *Fusarium culmorum* and characterized. The protein, termed FCWP1, demonstrated significant antifungal activity against several fungal species. Mutations in proteolytic consensus sequences contained within FCWP1 improved the stability of its antifungal activity. In addition, a class of proteins related to FCWP1 was identified and characterized. This class is made up of ribosomal proteins and displayed similar values for pI and molecular weight. A representative number of proteins from this class were tested and found to have significant antifungal activities.

The antifungal proteins disclosed herein are useful in controlling fungal infections in plants. Transgenic plants may be produced that are more resistant to fungal infections relative to non-transgenic plants of the same species. Alternatively, the proteins may be applied to plants exogenously.

20 Claims, 7 Drawing Sheets

```
GGGGGGGGGGGGGTGACAANTTCATCAACGAAACGATNTCACCCCCAGTTTTCCAC
CGTCAACACACCCAGAGACCATCACGACAATCGGCAAAAATGGCGACAACGACTCTCCCGTCACC
                                  M  A  D  N  D  S  P  V  T
CTCCGAACTCGCAAGTTCATCCGCAACCCTCTGCTGGGCCGTAAGCAGATGGTCGTTGACATCCTC
 L  R  T  R  K  F  I  R  N  P  L  L  G  R  K  Q  M  V  V  D  I  L
CACCCCAACCGTGCCAACATCTCCAAGGAGGAGCTCCGCGAGAAGCTCGGTTCCCCTACAAGGCC
 H  P  N  R  A  N  I  S  K  E  E  L  R  E  K  L  G  S  P  Y  K  A
CAGAAGGACCAGATCTCCGTCTTCGGTCTCCGAACCCAGTTCGGTGGCAAGACCACCGGCTTC
 Q  K  D  Q  I  S  V  F  G  L  R  T  Q  F  G  G  G  K  T  T  G  F
GCTCTCGTCTATGACTCCCCCGAGGCCATGAAGAAGTTCGAGCCTCAGTACCGATTGGTGCGCGTT
 A  L  V  Y  D  S  P  E  A  M  K  K  F  E  P  Q  Y  R  L  V  R  V
GGCCTCGCCACCAAGGCCGAGCGTGCTTCCCGACAGCAGCGCAAGAACGACAAAAG
 G  L  A  T  K  A  E  R  A  S  R  Q  Q  R  K  N  R  Q  K
ACTCTCCGAGGTACGGCAAAGTCAAGGGTGCCAAGGCGAAGAAGGAGAAATAAACGATTCATGGC
 T  L  R  G  T  A  K  V  K  G  A  K  A  K  K  E  K  *
TTGGCTTGTGTATATCCTCGGGCTGCTGGTTGGGGAGCGGCTGCTGCTGCTATGTCTGCAGCTGCCTGCATT
CGGTGGTCATGCGGGTGCGTCCATTACTACGGTCCATCCTCGTCGTCGGCGTCGGCTTTGGCATA
GGGTACAGGGACTTGCTGGCGGACGCGGGGCTATCTGGACTCGACGAGGGGGTTGAAGGCTACG
CTTTCACCTTCCTTGCTCAATACACTAGCATGAAATCAATGGTGTTTTTCGGGTTTTCGGACCAAAA
ACAAAAAATAGCAATGTCTCTGGTTTTCACGAAAAAAAAAAAAAAAAAAA
```

Figure 3

```
RPG19  MNDQPWMDSEWMQKMRTKRADAAVTIRTRKFLTNRLLQRK
FCWP              MADN..DSPVTLRTRKFIRNPLLGRK
                      *  *  ** ***** ***** ***

RPG19  QMVVDVIHPGLANVSKDELRSKIGKMYKADKEVVSVFGFKT
FCWP   QMVVDILHPNRANISKEELREKLGSPYKAQKDQISVFGLRT
       ****** ** ** **** **** *   **  ** ****  *

RPG19  HFGGGKTTGFALIYDNVEALKNFEPKHRLVRIGLA.EAPKG
FCWP   QFGGGKTTGFALVYDSPEAMKKFEPQYRLVRVGLATKAERA
        *********** ** **  * ****  **** ***  *

RPG19  GRKQRKEKKNREKKFRG...VRKSKKPRKE*
FCWP   SRQQRKQRKNRQKTLRGTAKVKGAKAKKEK*
        * *** ***  ***    *    * **

Figure 4
```

ANTIFUNGAL PROTEINS AND METHODS FOR THEIR USE

This application is a divisional of U.S. application Ser. No. 09/732,210, filed Dec. 7, 2000, now U.S. Pat. No. 6,573,361, which claims priority of U.S. Provisional Application No. 60/169,340, filed Dec. 7, 1999, and U.S. Provisional Application No. 60/169,513, filed Dec. 7, 1999.

FIELD OF THE INVENTION

The present invention relates to antifungal proteins and methods for their use. Specifically, the invention discloses novel antifungal proteins, nucleic acid sequences encoding the antifungal proteins, transformed host cells and transgenic plants expressing the antifungal proteins and useful for producing the antifungal proteins, as well as compositions containing the antifungal proteins. Methods are also disclosed for preparing the transformed host cells and transgenic plants.

INCORPORATION OF SEQUENCE LISTING

This application contains a sequence listing, which is contained on three identical CD-ROMs: two copies of a sequence listing (Copy 1 and Copy 2) and a sequence listing Computer Readable Form (CRF), all of which are herein incorporated by reference. All three CD-ROMs each contain one file called "SequenceListing_38-21(15036)C_v_Mar_30_2006.txt" which is 1,822,269 bytes in size and was created on Mar. 29, 2006.

BACKGROUND OF THE INVENTION

Protection of important crops from disease is a paramount objective of the agricultural industry because fungal infections cause significant economic losses in crops. Many plants have developed natural resistance to some pathogenic fungi. However, natural plant defenses often do not provide sufficient protection against fungal disease.

Fungi of multiple genera may cause disease or damage in plants. These genera include *Alternaria, Ascochyta, Aspergillus, Botrytis, Cercospora, Colletotrichum, Diplodia, Erysiphe, Fusarium, Gaeumanomyces, Helminthosporium, Macrophomina, Mycosphaerella, Nectria, Peronospora, Phoma, Phymatotrichum, Phytophthora, Plasmopara, Podosphaera, Puccinia, Puthium, Pyrenophora, Pyricularia, Pythium, Rhizoctonia, Scerotium, Sclerotinia, Septoria, Thielaviopsis, Uncinula, Venturia,* and *Verticillium*.

Many chemical fungicidal compounds have been developed to combat these various fungal pathogens. Examples of chemical antifungal agents include polyoxines, nikkomycines, carboxyamides, aromatic carbohydrates, carboxines, morpholines, inhibitors of sterol biosynthesis, and organophosphorus compounds (Worthington and Walker, 1983). The activity of these compounds is typically limited to several species or genera of fungi. As a consequence of the large number and diversity of pathogenic fungi, these compounds have not provided an effective solution to limiting fungal infections in plants.

An alternative approach to controlling fungal infections in plants involves identifying and developing biological compounds with antifungal activity. Identification of such compounds involves screening various organisms, such as plants and microbes, for agents possessing antifungal activity. Extracts are prepared from the organisms and tested in an in vitro antifungal assay. The antifungal agents can then be isolated from the extracts and further characterized. Several classes of antifungal proteins have been identified in this manner including chitinases, defensins, cysteine-rich chitin-binding proteins, β-1,3-glucanases, permatins (including zeamatins), thionins, ribosome-inactivating proteins, and non-specific lipid transfer proteins (Bowles, 1990; Brears et al., 1994, Broekaert et al., 1997).

A number of publications have described methods of using antifungal proteins from plants and bacteria in transgenic plants. The antifungal proteins used in these methods include glucanases, chitinases, osmotin-like proteins, and lysozymes produced in transgenic plants exhibiting increased resistance to various microorganisms (EP 0 292 435, EP 0 290 123, WO 88/00976, U.S. Pat. No. 4,940,840, WO 90/07001, EP 0 392 225, EP 0 307 841, EP 0 332 104, EP 0 440 304, EP 0 418 695, EP 0 448 511, WO 91/06312, WO 93/05153, and WO 91/18984).

Recombinant DNA technology has led to the development of transgenic plants that can produce antimicrobial proteins. The process generally involves transforming a plant tissue with a nucleic acid sequence encoding an antifungal protein, inducing the formation of transgenic tissue, and regenerating a plant from the transgenic tissue. Techniques for transformation of dicots are reviewed in Gasser and Fraley (1989). Monocot transformation and plant regeneration are reviewed in Davey et al. (1986) and Davey et al. (1989).

The antifungal activity of some of these proteins is dramatically reduced in the presence of 1 mM $CaCl_2$ and 50 mM KCl (Terras et al., 1992). Metal ions, such $K^+$, $Na^+$, $Ca^{2+}$, and $Mg^{2+}$, are required for normal physiological functions of plants and are abundant in plant cells. For an antifungal protein to be useful, it must maintain its antifungal activity in the presence of these ions. As a result, many of the proteins demonstrating antifungal activity in vitro are not efficacious in vivo.

Thus, there exists a need in the art for new classes of antifungal proteins, particularly those that exhibit antifungal activity against a large variety of pathogens and maintain that activity under the in vivo conditions of a plant.

SUMMARY OF THE INVENTION

The invention relates to antifungal proteins, and methods for their use. Specifically, the invention encompasses antifungal proteins, nucleic acid sequences encoding the antifungal proteins, transformed host cells and transgenic plants expressing the antifungal proteins and useful for producing the antifungal proteins, and compositions containing the antifungal proteins. Methods are also disclosed for preparing the transformed host cells and transgenic plants.

A novel antifungal protein, isolated from *Fusarium culmorum*, is disclosed. This protein, termed FCWP1, displays significant antifungal activity against a variety of fungal species. By altering a proteolytic consensus sequence contained within FCWP1, new variants are produced with improved stability of the antifungal activity.

A novel class of antifungal proteins related to FCWP1 is also disclosed. The proteins in this class are ribosomal proteins and have similar values for pI and molecular weight. A representative number of proteins from this class were tested and found to possess significant antifungal activities.

The antifungal proteins disclosed herein are useful in controlling fungal infections in plants. Transgenic plants may be produced that are more resistant to fungal infections relative to non-transgenic plants of the same species. Alternatively, the proteins may be applied to plants exogenously.

DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

The elements contained in the Figures illustrating plasmids are defined as follows: AMP: β-Lactamase; ori-pUC: replication origin derived from pUC plasmid; LAC: partial sequence of the Lac Z coding sequence; p-e35S: promoter e35S; HSP70 intron: the intron of heat shock protein 70 from maize; NOS3': 3' untranslated region of the nopaline synthase (nos) coding sequence of Agrobacterium Ti plasmid; ori-M13: M13 phage replication origin; Spc/Str: aminoglycoside adenyl transferase; p-FMV: figwort mosaic virus 35S promoter; EPSPS/CTP2: chloroplast transit peptide from the Arabidopsis 5-enolpyruvyl-3-phosphoshikimate synthase coding sequence (EPSPS); CP4 syn: synthetic bacterial glyphosate resistance coding sequence (CP4/5-enolpyruvyl-3-phosphoshikimate synthase); E9 3': 3' untranslated region of the pea ssRUBISCO E9 coding sequence; PetHSP70-Leader: 5' untranslated leader sequence of petunia heat shock protein 70 coding sequence; ori-322: pUC322 replication origin; ori V: the vegetative origin of replication; rop: coding region for the repressor of primer; Left Border: octopine left border; Right Border: sequence essential for transfer T-DNA; AlyAFP: antifungal protein from alyssum flower; alysigsynFCWP1: signal peptide from AlyAFP fused to the synthetic coding sequence of Fusarium culmorum antifungal protein (FCWP1).

FIG. 3 shows the FCWP1 cDNA (SEQ ID NO:18) translation (SEQ ID NO:1754).
FIG. 4 is a sequence alignment of the cDNA translation of FCWP1 (SEQ ID NO:1754) and the yeast ribosomal protein RPG19 (SEQ ID NO:1564).

DESCRIPTION OF SEQUENCES

Figure 1:
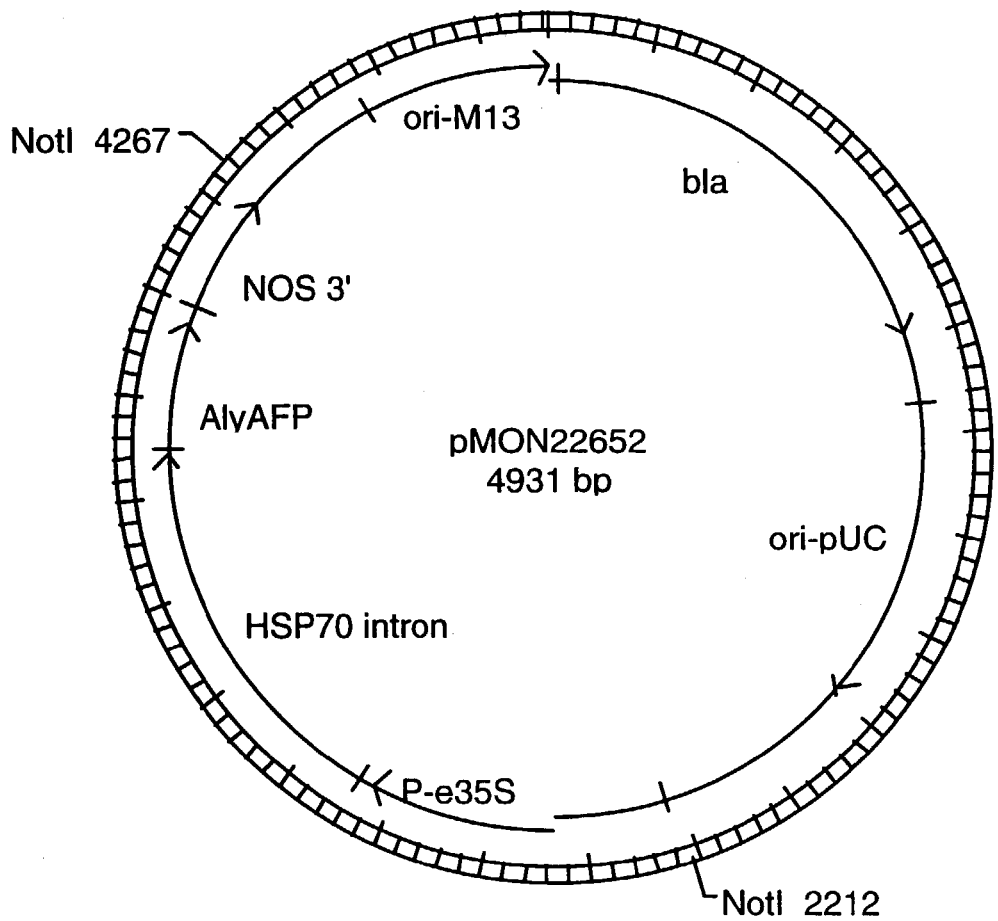
FIG. 1 is a plasmid map of pMON22652.

The following sequence listings form part of the present specification and are included to further demonstrate certain aspects of the present invention. The invention may be better understood by reference to one or more of these sequences in combination with the detailed description of specific embodiments presented herein.

| SEQ ID NO: | Description |
| --- | --- |
| 1 | FCWP 1 amino acid sequence |
| 2 | fcwp1 nucleic acid coding sequence |
| 3 | fcwp1.5, 75-mer (Example 6) |
| 4 | fcwp1.6, 77-mer (Example 6) |
| 5 | fcwp1.7, 29-mer (Example 6) |
| 6 | fcwp1.8, 29-mer (Example 6) |
| 7 | AlyAFP, 38-mer (Examples 7, 20) |

-continued

| SEQ ID NO: | Description |
| --- | --- |
| 8 | AlyAFP, 41-mer (Example 7) |
| 9 | fcwp1.9, 20-mer (Example 7, 11) |
| 10 | fcwp1.10, 30-mer (Example 7, 11) |
| 11 | AlyAFP signal/fcwp1 fusion |
| 12 | fcwp1.4, 34-mer (Example 10) |
| 13 | PolyG-RI, 30-mer (Example 10) |
| 14 | 5' fcwp1 cDNA sequence |
| 15 | CAR 61, 37-mer (Example 11) |
| 16 | Poly-T, 32-mer (Example 11) |
| 17 | 3' fcwp1 cDNA sequence |
| 18 | fcwp1 full length cDNA sequence |
| 19 | FCWP2 amino acid sequence |
| 20 | FCWP3 amino acid sequence |
| 21 | FCWP4 amino acid sequence |
| 22 | FCWP5 amino acid sequence |
| 23 | FCWP6 amino acid sequence |
| 24 | FCWP7 amino acid sequence |
| 25 | FCWP2 Oligomer (Example 20) |
| 26 | FCWP3 Oligomer (Example 20 |
| 27 | FCWP4 Oligomer (Example 20) |
| 28 | FCWP5 Oligomer (Example 20) |
| 29 | FCWP6 Oligomer (Example 20) |
| 30 | FCWP7 Oligomer (Example 20) |
| 31 | BL-32, B. rapa chloroplast ribosomal protein |
| 32 | BL-36, Black pine chloroplast ribosomal protein |
| 33 | SL-23, Spinach chloroplast ribosomal protein |
| 34 | YL-46, Yeast ribosomal protein |
| 35 | YL-41, Yeast ribosomal protein |
| 36 | BL-36 synthetic DNA sequence for wheat |
| 37 | BL-36 synthetic DNA sequence for potato |
| 38-1753 | ribosomal protein sequences; calculated pI > 7 and MW <20 kDa |

DEFINITIONS

The following definitions are provided in order to aid those skilled in the art in understanding the detailed description of the present invention.

"Antifungal" refers to an activity that kills, inhibits, or disrupts fungal growth. This activity may target sporulation, mating, or spore germination. The antifungal activity may also interfere with the normal development of fungal cells by disrupting or retarding any stage of the fungal lifecycle.

"Antigenic epitope" refers to any discrete segment of a molecule, protein, or nucleic acid capable of eliciting an immune response, wherein the immune response results in the production of antibodies reactive with the antigenic epitope.

"Coding sequence" and "open reading frame" refer to a region of continuous sequential nucleic acid triplets encoding a protein, polypeptide, or peptide sequence.

"Hybridization" refers to the ability of a strand of nucleic acid to join with a complementary strand via base pairing. Hybridization occurs when complementary sequences in the two nucleic acid strands bind to one another.

"Identical" nucleotide or protein sequences are determined by using programs such as GAP or BestFit from GCG (Genetics Computer Group, Inc., Madison, Wis.) using the default parameters.

"Nucleic acid" refers to deoxyribonucleic acid (DNA) and ribonucleic acid (RNA).

"Phenotype" refers to traits exhibited by an organism resulting from the interaction of genotype and environment.

"pI" refers to the pH value at which a protein or peptide has no net overall charge. At pH values below the pI, the protein or peptide will be positively charged, and at pH values above the pI, the protein or peptide will be negatively charged.

"Polyadenylation signal" or "polyA signal" refers to a nucleic acid sequence located 3' to a coding region that promotes the addition of adenylate nucleotides to the 3' end of the mRNA transcribed from the coding region.

"Promoter" or "promoter region" refers to a nucleic acid sequence, usually found upstream (5') to a coding sequence, that controls expression of the coding sequence by controlling production of messenger RNA (mRNA) by providing the recognition site for RNA polymerase or other factors necessary for start of transcription at the correct site.

"Recombinant nucleic acid vector" refers to any agent such as a plasmid, cosmid, virus, autonomously replicating sequence, phage, or linear or circular single-stranded or double-stranded DNA or RNA nucleotide segment, derived from any source, capable of genomic integration or autonomous replication, comprising a nucleic acid molecule in which one or more nucleic acid sequences have been linked in a functionally operative manner. Such recombinant nucleic acid constructs or vectors are capable of introducing a 5' regulatory sequence or promoter region and a DNA sequence for a selected gene product into a cell in such a manner that the DNA sequence is transcribed into a functional mRNA, which is subsequently translated into a polypeptide or protein. Recombinant nucleic acid constructs or recombinant vectors may be constructed to be capable of expressing antisense RNAs, in order to inhibit translation of a specific RNA of interest.

"Regeneration" refers to the process of growing a plant from a plant cell (e.g., plant protoplast or explant).

"Ribosomal protein" refers to a protein, polypeptide, or peptide found in association with a ribosome in vivo.

"Selectable marker" refers to a nucleic acid sequence whose expression confers a phenotype facilitating identification of cells containing the nucleic acid sequence. Selectable markers include those that confer resistance to toxic chemicals (e.g., ampicillin resistance, kanamycin resistance), complement a nutritional deficiency (e.g., uracil, histidine, leucine), or impart a visually distinguishing characteristic (e.g., color changes or fluorescence).

"Transcription" refers to the process of producing an RNA copy from a DNA template.

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

"Transgenic" refers to organisms into which exogenous nucleic acid sequences are integrated.

"Vector" refers to a plasmid, cosmid, bacteriophage, or virus that carries exogenous DNA into a host organism.

DETAILED DESCRIPTION OF THE INVENTION

The invention relates to antifungal proteins and methods for their use. Specifically, the invention encompasses antifungal proteins, nucleic acid sequences encoding the antifungal proteins, transformed host cells and transgenic plants expressing the antifungal proteins and useful for producing the antifungal proteins, and compositions containing the antifungal proteins. Methods are also disclosed for preparing the transformed host cells and transgenic plants.

Protein Sequences

The invention is directed to a protein that preferably is at least about 85% identical to SEQ ID NO:1, more preferably is at least about 86%, 87%, 88%, 89%, 90%, 91%, 92%, 93%, 94%, 95%, 96%, 97%, 98%, or 99% identical to SEQ ID NO:1, and most preferably is SEQ ID NO:1.

To further aid in the study and application of the protein of SEQ ID NO:1, antibodies may be prepared. These antibodies may be raised against any portion of the protein that provides an antigenic epitope. The antibodies may be polyclonal or monoclonal. Such an antibody is preferably immunoreactive with SEQ ID NO:1.

The protein that is at least about 85% to 100% identical to SEQ ID NO:1 is preferably reactive with such antibodies.

The antibodies may be used to detect the presence of SEQ ID NO:1 by ELISA, radioimmunoassay, immunoblot, western blot, immunofluorescence, immuno-precipitation, or any other comparable technique. In addition, a kit may be designed that incorporates one or more of these techniques that use the antibodies described above to detect SEQ ID NO:1.

Nucleic Acid Sequences

The invention is also directed to a nucleic acid segment comprising a nucleic acid sequence encoding a protein at least about 85% identical to SEQ ID NO:1, more preferably encoding a protein at least about 86%, 87%, 88%, 89%, 90%, 91%, 92%, 93%, 94%, 95%, 96%, 97%, 98%, or 99% identical to SEQ ID NO:1, and most preferably encoding SEQ ID NO:1.

Alternatively, the nucleic acid sequence is preferably at least about 85% identical to SEQ ID NO:2, more preferably is at least about 86%, 87%, 88%, 89%, 90%, 91%, 92%, 93%, 94%, 95%, 96%, 97%, 98%, or 99% identical to SEQ ID NO:2, and most preferably is SEQ ID NO:2.

Alternatively, the nucleic acid sequence is preferably at least about 85% identical to SEQ ID NO:18, more preferably is at least about 86%, 87%, 88%, 89%, 90%, 91%, 92%, 93%, 94%, 95%, 96%, 97%, 98%, or 99% identical to SEQ ID NO:18, and most preferably is SEQ ID NO:18.

The structural nucleic acid sequences may be obtained (i.e., cloned or isolated) from various species of plants, animals, bacteria, and fungi and utilized in the present invention. Preferably, the structural nucleic acid sequence is derived from a plant, fungal, or bacterial source or is chemically synthesized.

Nucleic Acid Hybridization

The nucleic acid sequence may be further identified by its ability to hybridize with a complementary sequence. Nucleic acid hybridization is a technique well known to those of skill in the art of DNA manipulation. The hybridization properties of a given pair of nucleic acids are an indication of their similarity or identity.

Low stringency conditions may be used to select sequences with lower sequence identities to a target sequence. One may wish to employ conditions such as about 0.15 M to about 0.9 M sodium chloride, at temperatures ranging from about 20° C. to about 55° C.

High stringency conditions may be used to select for nucleic acid sequences with higher degrees of identity to the disclosed sequences (Sambrook et al., 1989). The high stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. The high stringency conditions are preferably provided by 6×SSC, 5×Denhardt's solution, 100 mg/mL fish sperm DNA, and 0.1% (w/v) SDS, with an incubation at 55° C. for several hours.

The hybridization is generally followed by several wash steps. The wash compositions generally comprise 0.5× to about 10×SSC, and 0.01% (w/v) to about 0.5% (w/v) SDS with a 15-minute incubation at about 20° C. to about 70° C. Preferably, the nucleic acid segments remain hybridized after washing at least one time in 0.1×SSC at 65° C.

The nucleic acid sequence preferably hybridizes, under low or high stringency conditions, with SEQ ID NO:2, or the complement thereof. Alternatively, the nucleic acid sequence preferably hybridizes, under low or high stringency conditions, with SEQ ID NO:18, or the complement thereof.

Related Antifungal Proteins

Additional proteins, similar to SEQ ID NO:1 with respect to molecular weight and pI, were identified and characterized. These were found to also have antifungal activity. These antifungal proteins generally have a small molecular weight and a high pI and are ribosomal proteins. The pI preferably is greater than about 7, more preferably is greater than about 10, and most preferably is greater than about 11.5. The molecular weight preferably is between about 2 kDa and about 20 kDa, more preferably is between about 2 kDa and about 15 kDa, and most preferably is between about 3 kDa and about 7 kDa.

Nucleic Acid Sequences Encoding the Related Antifungal Proteins

Nucleic acid segments comprising nucleic acid sequences encoding the aforementioned antifungal proteins may be obtained. Such nucleic acid sequences preferably encode an antifungal ribosomal protein having a pI that is greater than about 7, more preferably is greater than about 10, and most preferably is greater than about 11.5. The nucleic acid also may encode an antifungal protein with a molecular weight that is preferably between about 2 kDa and about 20 kDa, more preferably is between about 2 kDa and about 15 kDa, and most preferably is between about 3 kDa and about 7 kDa.

The nucleic acid sequence may encode an antifungal protein at least about 85% identical to SEQ ID NOS: 19, 20, 21, 22, 23, 24, 31, 32, 33, 34, or 35, more preferably encode an antifungal protein at least about 86%, 87%, 88%, 89%, 90%, 91%, 92%, 93%, 94%, 95%, 96%, 97%, 98%, or 99% identical to SEQ ID NOS: 19, 20, 21, 22, 23, 24, 31, 32, 33, 34, or 35, and most preferably encode SEQ ID NOS: 19, 20, 21, 22, 23, 24, 31, 32, 33, 34, or 35.

The structural nucleic acid sequences may be obtained (i.e., cloned or isolated) from various species of plants, animals, bacteria, and fungi and utilized in the present invention. Preferably, the structural nucleic acid sequence is derived from a plant, fungal, or bacterial source or is chemically synthesized.

The above mentioned nucleic acid sequences may be provided in a variety of forms. For instance, the nucleic acid sequence may be contained within a segment of cDNA, genomic DNA, synthetic DNA, or plasmid DNA. Alternatively, the nucleic acid sequence may be contained in an RNA molecule. Each of these forms of nucleic acid will preferably encode an antifungal protein as disclosed in the present invention. These different forms may be utilized to produce recombinant vectors, transformed host cells, and transgenic plants.

Fusion Proteins

Fusion proteins may be constructed that comprise an antifungal protein and a fusion partner comprising at least one additional amino acid, peptide, or protein. Many possible fusion partners exist. For instance, the fusion partner may provide a "tagged" epitope to facilitate detection of the protein. Alternatively, the fusion partner may provide a regulatory, enzymatic, or intercellular transport function. SEQ ID NO:11 demonstrates a fusion product of the SEQ ID NO:2 with a nucleic acid encoding a signal peptide of an antifungal protein isolated from *Alyssum* (AlyAFP1) (U.S. Pat. No. 5,773,696).

The pI of the antifungal ribosomal protein contained within the fusion protein preferably is greater than about 7, more preferably is greater than about 10, and most preferably is greater than about 11.5. The molecular weight of the antifungal protein preferably is between about 2 kDa and about 20 kDa, more preferably is between about 2 kDa and about 15 kDa, and most preferably is between about 3 kDa and about 7 kDa.

Alternatively, the antifungal protein within the fusion protein is at least about 85% identical to SEQ ID NO:1, more preferably is at least about 86%, 87%, 88%, 89%, 90%, 91%, 92%, 93%, 94%, 95%, 96%, 97%, 98%, or 99% identical to SEQ ID NO:1, and most preferably is SEQ ID NO:1.

The fusion protein comprising an amino acid sequence at least between about 85% and about 100% identical with SEQ ID NO:1 is preferably reactive with an antibody raised against an antigenic epitope from SEQ ID NO:1.

The antifungal protein may also preferably be at least about 85% identical to SEQ ID NOS: 19, 20, 21, 22, 23, 24, 31, 32, 33, 34, or 35, more preferably at least about 86%, 87%, 88%, 89%, 90%, 91%, 92%, 93%, 94%, 95%, 96%, 97%, 98%, or 99% identical to SEQ ID NOS: 19, 20, 21, 22, 23, 24, 31, 32, 33, 34, or 35, and most preferably is SEQ ID NOS: 19, 20, 21, 22, 23, 24, 31, 32, 33, 34, or 35.

Codon Usage

Due to the degeneracy of the genetic code, different nucleotide codons may be used to code for a particular amino acid. A host cell often displays a preferred pattern of codon usage (Campbell et al., 1990). Nucleic acid sequences are preferably constructed to utilize the codon usage pattern of the particular host cell. This generally enhances the expression of the nucleic acid sequence in a transformed host cell. The nucleic acid sequences disclosed herein preferably utilize the optimal codon usage for bacterial, fungal, and plant host cells.

Modifications of Nucleic Acid Sequences Encoding Antifungal Proteins

Variations in the nucleic acid sequence encoding an antifungal protein may lead to mutant antifungal protein sequences that display equivalent or superior antifungal characteristics when compared to the sequences disclosed herein. Mutations may include deletions, insertions, truncations, substitutions, fusions, shuffling of subunit sequences, and the like.

Mutations to a nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a nucleic acid sequence. Examples include single strand rescue (Kunkel, 1985), unique site elimination (Deng and Nickloff, 1992), nick protection (Vandeyar et al., 1988), and PCR (Costa et al., 1996). Random or non-specific mutations may be generated by chemical agents (for a general review, see Singer and Kusmierek, 1982) such as nitrosoguanidine (Cerda-Olmedo et al., 1968; Guerola et al., 1971) and 2-aminopurine (Rogan and Bessman, 1970), or by biological methods such as passage through mutator strains (Greener et al., 1997).

The modifications may result in either conservative or non-conservative changes in the amino acid sequence. Conservative changes result from additions, deletions, substitutions, etc. in the nucleic acid sequence that do not alter the final amino acid sequence of the protein. Non-conservative changes include additions, deletions, and substitutions that result in an altered amino acid sequence.

Additional methods of making the alterations described above are described by Ausubel et al. (1995); Bauer et al. (1985); Craik (1985); Frits Eckstein et al. (1982); Sambrook et al. (1989); Smith et al. (1981); Osuna et al. (1994); and Walder et al. (1986).

Modification and changes may be made in the sequence of the proteins of the present invention and the nucleic acid segments that encode them and still obtain a functional molecule that encodes a protein with desirable antifungal properties. The following is a discussion based upon changing the amino acid sequence of a protein to create an equivalent, or possibly an improved, second-generation molecule. The amino acid changes may be achieved by changing the codons of the nucleic acid sequence, according to the codons given in Table 1.

TABLE 1

Codon degeneracies of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATG ATT |
| Lysine | K | Lys | AAA AAG |
| Leucine | L | Leu | TTA TTG CTA CTG CTG CTT |
| Methionine | M | Met | ATG |
| Asparagine | N | Asn | AAC AAT |
| Proline | P | Pro | CCA CCC CCG CCT |
| Glutamine | Q | Gln | GAA GAG |
| Arginine | R | Arg | AGA AGG CGA CGG GGG CGT |
| Serine | S | Ser | AGC AGT TCA TGC TCG TCT |
| Threonine | T | Thr | ACA ACC ACG ACT |
| Valine | V | Val | GTA GTG GTG GTT |
| Tryptophan | W | Trp | TGG |
| Tyrosine | Y | Tyr | TAC TAT |

Certain amino acids may be substituted for other amino acids in a protein sequence without appreciable loss of enzymatic activity. It is thus contemplated that various changes may be made in the peptide sequences of the disclosed protein sequences, or their corresponding nucleic acid sequences, without appreciable loss of the biological activity.

In making such changes, the hydropathic index of amino acids may be considered. The importance of the hydropathic amino acid index in conferring interactive biological function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics. These are isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine, and isoleucine. Changes that are not expected to be advantageous may also be used if these resulted in functional antifungal proteins.

Sequence Analysis

In the present invention, sequence similarity or identity can be determined using the "BestFit" or "Gap" programs of the Sequence Analysis Software Package, Genetics Computer Group, Inc., University of Wisconsin Biotechnology Center, Madison, Wis. 53711. The programs were used with the default parameters.

Proteins falling in the class of antifungal proteins described were identified by searching in the public sequence databases using the search string "ribosom." The software used for searching was the LookUp program supplied with GCG version 9.1 (Genetics Computer Group, Inc., Madison, Wis.). The set of sequences returned was edited by a biologist to eliminate sequences that were not ribosomal proteins. The edited set was then searched using IsoSearch, a computer program written at Monsanto that calculates the mass and predicted pI of proteins, for proteins with a pI>7 and a molecular mass <20 kDa. (Monsanto Company, St. Louis, Mo.)

The predicted isoelectric point (pI) of each protein was calculated using the HasIsoPoint algorithm in GCG version 9.1 (supplied as Fortran code but rewritten in C). This algorithm, written originally by L. L. Houston and rewritten by Frank J. Manion of the Fox Chase Cancer Center, Philadelphia, Pa., uses a binary search that assumes the net charge of a protein is a monotonic decreasing function over the pH range from pH 1.0 to pH 13.0.

pK data was obtained from the isoelectric.dat table supplied with GCG version 9.1, based upon Bull (An Introduction to Physical Biochemistry, 1964).

Protein mass was calculated using the average atomic masses of unhydrated amino acids derived from the aafreq-.dat table supplied with GCG version 9.1.

Recombinant Vectors

Any of the above mentioned structural nucleic acid sequences may be used to prepare a recombinant vector. The recombinant vector typically comprises, in a 5' to 3' orientation: a promoter to direct the transcription of a structural nucleic acid sequence, a structural nucleic acid sequence, a 3' transcriptional terminator, and a 3' polyadenylation signal. The recombinant vector may further comprise untranslated sequences, transit and targeting sequences, selectable markers, enhancers, or operators.

Means for preparing recombinant vectors are well known in the art. Methods for making recombinant vectors particularly suited to plant transformation are described in U.S. Pat. Nos. 4,971,908, 4,940,835, 4,769,061 and 4,757,011. These types of vectors have also been reviewed (Rodriguez et al., 1988; Glick et al., 1993).

Typical vectors useful for expression of nucleic acids in higher plants are well known in the art and include vectors derived from the tumor-inducing (Ti) plasmid of *Agrobacterium tumefaciens* (Rogers et al., 1987). Other recombinant vectors useful for plant transformation, including the pCaM-VCN transfer control vector, have also been described (Fromm et al., 1985).

Promoters

The selection of a suitable promoter depends on the type of host cell in which it will be used. Promoters that function in bacteria, yeast, and plants are all well taught in the art.

The promoter may also be selected on the basis of transcriptional regulation that it provides. Such regulation may include enhancement of transcriptional activity, inducibility, tissue specificity, and developmental stage specificity. In plants, promoters that are inducible, of viral or synthetic origin, constitutively active, and temporally regulated and spatially regulated have been described (Poszkowski et al., 1989; Odell et al., 1985; Chau et al., 1989).

Often-used constitutive promoters include the CaMV 35S promoter (Odell, 1985), the enhanced CaMV 35S promoter, the Figwort Mosaic Virus (FMV) promoter (Richins et al., 1987), the mannopine synthase (mas) promoter, the nopaline synthase (nos) promoter, and the octopine synthase (ocs) promoter.

Useful inducible promoters include promoters induced by salicylic acid or polyacrylic acids (PR-1, Williams, 1992), induced by application of safeners (substituted benzenesulfonamide herbicides, Hershey, 1991), heat-shock promoters (Ou-Lee et al., 1986; Ainley et al., 1990), a nitrate-inducible promoter derived from the spinach nitrite reductase sequence (Back et al., 1991), hormone-inducible promoters (Yamaguchi-Shinozaki et al., 1990; Kares et al., 1990), and light-inducible promoters associated with the small subunit of RuBP carboxylase and LHCP families (Kuhlemeier et al., 1989; Feinbaum et al., 1991; Weisshaar et al., 1991; Lam and Chua, 1990; Castresana et al., 1988; Schulze-Lefert et al., 1989).

Examples of useful tissue-specific, developmentally regulated promoters include the β-conglycinin 7S promoter (Doyle et al., 1986; Slighton and Beachy, 1987) and seed-specific promoters (Knutzon et al., 1992; Bustos et al., 1991; Lam and Chua, 1991; Stayton et al., 1991). Plant functional promoters useful for preferential expression in seed plastids include those from plant storage proteins and from proteins involved in fatty acid biosynthesis in oilseeds. Examples of such promoters include the 5' regulatory regions from such sequences as napin (Kridl et al., 1991), phaseolin, zein, soybean trypsin inhibitor, ACP, stearoyl-ACP desaturase, and oleosin. Seed-specific regulation is discussed in EP 0 255 378.

Another exemplary tissue-specific promoter is the lectin promoter, which is specific for seed tissue. The lectin protein in soybean seeds is encoded by a single nucleic acid sequence (Le1) that is only expressed during seed maturation and accounts for about 2% to about 5% of total seed mRNA. The lectin nucleic acid sequence and seed-specific promoter have been fully characterized and used to direct seed-specific expression in transgenic tobacco plants (Vodkin et al., 1983; Lindstrom et al., 1990.)

A suitable promoter may also be induced during a plant defense response against a fungal infection. Typically, a fungal infection triggers an induction of a large number of pathogenesis-related (PR) proteins by the infected plant (Bowles, 1990; Bol et al., 1990; Linthorst, 1991). Such PR proteins may be enzymes involved in phenylpropanoid metabolism (e.g., phenylalanine ammonia lyase, chalcone synthase), proteins that modify plant cell walls (e.g., hydroxyproline-rich glycoproteins, glycine-rich proteins, peroxidases), enzymes that degrade fungal cell walls (e.g., chitinases, glucanases), thaumatin-like proteins, or proteins with as yet unknown functions.

The promoters of these PR sequences may be obtained and utilized in the present invention. Isolation of these PR promoters has been reported from potato plants (Fritzemeier et al., 1987; Cuypers et al., 1988; Logemann et al., 1989; Matton et al., 1989; Schroder et al., 1992) and tobacco plants (Martini et al., 1993).

Promoter hybrids can also be constructed to enhance transcriptional activity (Comai, L. and Moran, P. M., U.S. Pat. No. 5,106,739, issued Apr. 21, 1992), or to combine desired transcriptional activity and tissue specificity.

Promoters having particular utility in the present invention include the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco (Mandel et al., 1995); corn sucrose synthetase 1 (Yang and Russell, 1990); corn alcohol dehydrogenase 1 (Vogel et al., 1989); corn light harvesting complex (Simpson, 1986); corn heat shock protein (Odell et al., 1985); the chitinase promoter from *Arabidopsis* (Samac et al., 1991); the LTP (Lipid Transfer Protein) promoters from broccoli (Pyee et al., 1995); petunia chalcone isomerase (Van Tunen et al., 1988); bean glycine rich protein 1 (Keller et al., 1989); potato patatin (Wenzler et al., 1989); the ubiquitin promoter from maize (Christensen et al., 1992); the sugarcane badnavirus promoter; the rice RC2 promoter; and the actin promoter from rice (McElroy et al., 1990). All of these promoters have been used to create various types of DNA constructs that have been expressed in plants. See, for example, PCT International Publication WO 84/02913 in this regard.

Structural Nucleic Acid Sequences

The structural nucleic acid sequence preferably encodes an antifungal ribosomal protein having a pI that is greater than about 7, more preferably is greater than about 10, and most preferably is greater than about 11.5. The nucleic acid also may encode an antifungal protein with a molecular weight that is preferably between about 2 kDa and about 20 kDa, more preferably is between about 2 kDa and about 15 kDa, and most preferably is between about 3 kDa and about 7 kDa.

The structural nucleic acid sequence may encode a protein at least about 85% identical to SEQ ID NO:1, more preferably encodes a protein at least about 86%, 87%, 88%, 89%, 90%, 91%, 92%, 93%, 94%, 95%, 96%, 97%, 98%, or 99% identical to SEQ ID NO:1, and most preferably encodes SEQ ID NO:1.

Alternatively, the nucleic acid sequence is preferably at least about 85% identical to SEQ ID NO:2, more preferably is at least about 86%, 87%, 88%, 89%, 90%, 91%, 92%, 93%, 94%, 95%, 96%, 97%, 98%, or 99% identical to SEQ ID NO:2, and most preferably is SEQ ID NO:2.

Alternatively, the nucleic acid sequence is preferably at least about 85% identical to SEQ ID NO:18, more preferably is at least about 86%, 87%, 88%, 89%, 90%, 91%, 92%, 93%, 94%, 95%, 96%, 97%, 98%, or 99% identical to SEQ ID NO:18, and most preferably is SEQ ID NO:18.

The structural nucleic acid sequence may be further identified by its ability to hybridize with a complementary sequence. Various conditions for nucleic acid hybridizations are well taught in the art (Sambrook et al., 1989; Ausubel et al., 1995). The structural nucleic acid sequence preferably hybridizes, under low or high stringency conditions, with SEQ ID NO:2, or the complement thereof. Alternatively, the structural nucleic acid sequence preferably hybridizes, under low or high stringency conditions, with SEQ ID NO:18, or the complement thereof.

Alternatively, the structural nucleic acid sequence may encode an antifungal protein at least about 85% identical to SEQ ID NOS: 19, 20, 21, 22, 23, 24, 31, 32, 33, 34, or 35, more preferably encode an antifungal protein at least about 86%, 87%, 88%, 89%, 90%, 91%, 92%, 93%, 94%, 95%, 96%, 97%, 98%, or 99% identical to SEQ ID NOS: 19, 20, 21, 22, 23, 24, 31, 32, 33, 34, or 35, and most preferably encode SEQ ID NOS: 19, 20, 21, 22, 23, 24, 31, 32, 33, 34, or 35.

The structural nucleic acid sequences may be obtained (i.e., cloned or isolated) from various species of plants, animals, bacteria, and fungi and utilized in the present invention. Preferably, the structural nucleic acid sequence is derived from a plant, fungal, or bacterial source or is chemically synthesized.

Other Elements of the Recombinant Vector

A 3' non-translated region typically provides a transcriptional termination signal and a polyadenylation signal that functions in plants to cause the addition of adenylate nucleotides to the 3' end of the mRNA. These may be obtained from the 3' regions to the nopaline synthase (nos) coding sequence, the soybean 7S storage protein coding sequence, and the pea ssRUBISCO E9 coding sequence, or from the Agrobacterium tumor-inducing (Ti) plasmid (Fischhoff et al., European Patent Application 0 385 962; U.S. Pat. No. 5,500,365).

The recombinant vector may further comprise a selectable marker. The nucleic acid sequence serving as the selectable marker functions to produce a phenotype in cells that facilitates their identification relative to cells not containing the marker. Useful selectable markers include GUS, green fluorescent protein (GFP), neomycin phosphotransferase II (nptII), luciferase (LUX), antibiotic resistance sequences, and herbicide (e.g., glyphosphate) tolerance sequences. The selectable marker is preferably a kanamycin, hygromycin, or herbicide resistance marker.

Typically, nucleic acid sequences located a few hundred base pairs downstream of the polyadenylation site serve to terminate transcription. These regions are required for efficient polyadenylation of transcribed mRNA.

The recombinant vector may further comprise a nucleic acid sequence encoding a transit peptide, such as the Alyssum signal peptide or the chloroplast transit peptide from Arabidopsis. This peptide may be useful for directing a protein to the extracellular space or to some other compartment inside or outside of the cell.

Translational enhancers may also be incorporated as part of the recombinant vector. Thus the recombinant vector may preferably contain one or more 5' non-translated leader sequences that serve to enhance expression of the nucleic acid sequence. Such enhancer sequences may be desirable to increase or alter the translational efficiency of the resultant mRNA.

Probes and Primers

Short nucleic acid sequences having the ability to specifically hybridize to complementary nucleic acid sequences may be produced and utilized in the present invention. These short nucleic acid molecules may be used as probes to identify the presence of a complementary sequence in a given sample. Thus, by constructing a nucleic acid probe that is complementary to a small portion of a particular nucleic acid sequence, the presence of that sequence may be assessed. Use of these probes may greatly facilitate the identification of transgenic plants that contain a particular nucleic acid sequence (e.g., a nucleic acid sequence encoding an antifungal protein). The probes may also be used to screen cDNA or genomic libraries for additional sequences encoding antifungal proteins.

Alternatively, the short nucleic acid sequences may be used as oligonucleotide primers to amplify or mutate a complementary nucleic acid sequence using PCR technology. These primers may also facilitate the amplification of related complementary sequences (e.g., related nucleic acid sequences from other species).

The primer or probe is generally complementary to a portion of the nucleic acid sequence that is to be identified, amplified, or mutated. The primer or probe should be of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long.

The primer or probe may be prepared by direct chemical synthesis, by PCR (U.S. Pat. Nos. 4,683,195, and 4,683, 202), or by excising the nucleic acid specific fragment from a larger nucleic acid molecule.

Transgenic Plants and Transformed Host Cells

The invention is also directed to transgenic plants and transformed host cells that comprise, in a 5' to 3' orientation: a promoter to direct the transcription of a structural nucleic acid sequence, a structural nucleic acid sequence, a 3' transcriptional terminator, and a 3' polyadenylation signal.

The structural nucleic acid sequence preferably encodes a ribosomal protein having a pI that is greater than about 7, more preferably is greater than about 10, and most preferably is greater than about 11.5. The structural nucleic acid encodes a protein with a molecular weight that is preferably between about 2 kDa and about 20 kDa, more preferably is between about 2 kDa and about 15 kDa, and most preferably is between about 3 kDa and about 7 kDa.

The promoter may be seed selective, tissue selective, constitutive, or inducible. Such promoters include the nopaline synthase (NOS), octopine synthase (OCS), mannopine synthase (mas), cauliflower mosaic virus 19S and 35S (CaMV19S, CaMV35S), enhanced CaMV (eCaMV), ribulose 1,5-bisphosphate carboxylase (ssRUBISCO), figwort mosaic virus (FMV), CaMV derived AS4, tobacco RB7 wheat POX1 promoter, tobacco EIF-4, lectin protein (Le1), and rice RC2 promoter.

The structural nucleic acid sequence encodes a protein at least about 85% identical to SEQ ID NO:1, more preferably encodes a protein at least about 86%, 87%, 88%, 89%, 90%, 91%, 92%, 93%, 94%, 95%, 96%, 97%, 98%, or 99% identical to SEQ ID NO:1, and most preferably encodes SEQ ID NO:1.

Alternatively, the structural nucleic acid sequence is preferably at least about 85% identical to SEQ ID NO:2, more preferably is at least about 86%, 87%, 88%, 89%, 90%, 91%, 92%, 93%, 94%, 95%, 96%, 97%, 98%, or 99% identical to SEQ ID NO:2, and most preferably is SEQ ID NO:2.

Alternatively, the structural nucleic acid sequence is preferably at least about 85% identical to SEQ ID NO:18, more preferably is at least about 86%, 87%, 88%, 89%, 90%, 91%, 92%, 93%, 94%, 95%, 96%, 97%, 98%, or 99% identical to SEQ ID NO:18, and most preferably is SEQ ID NO:18.

The structural nucleic acid sequence may be further identified by its ability to hybridize with a complementary sequence. Various conditions for nucleic acid hybridizations are well taught in the art (Sambrook et al., 1989; Ausubel et al., 1995). The structural nucleic acid sequence preferably hybridizes, under low or high stringency conditions, with SEQ ID NO:2, or the complement thereof. Alternatively, the structural nucleic acid sequence preferably hybridizes, under low or high stringency conditions, with SEQ ID NO:18, or the complement thereof.

Alternatively, the structural nucleic acid sequence may encode a protein at least about 85% identical to SEQ ID NOS: 19, 20, 21, 22, 23, 24, 31, 32, 33, 34, or 35, more preferably encode a protein at least about 86%, 87%, 88%, 89%, 90%, 91%, 92%, 93%, 94%, 95%, 96%, 97%, 98%, or 99% identical to SEQ ID NOS: 19, 20, 21, 22, 23, 24, 31, 32, 33, 34, or 35, and most preferably encode SEQ ID NO: 19, 20, 21, 22, 23, 24, 31, 32, 33, 34, or 35.

The transformed host cell may generally be any cell that is compatible with the present invention. The transformed host cell may be prokaryotic, such as a bacterial cell, and more preferably is a *Agrobacterium, Arthrobacter, Azospyrillum, Clavibacter, Escherichia, Pseudomonas,* or *Rhizobacterium* cell. The transformed host cell preferably is eukaryotic, and more preferably is a plant, yeast, or fungal cell. If a yeast cell is selected to be transformed, it preferably is a *Saccharomyces cerevisiae, Schizosaccharomyces pombe,* or *Pichia pastoris.* If a plant cell is selected to be transformed, it may be of any type capable of being transformed, preferably one with an agronomic, horticultural, ornamental, economic, or commercial value and more preferably is an *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, or zucchini cell.

A transgenic plant is then preferably regenerated from the transformed cell using routine techniques available to one skilled in the art. The resulting transgenic plant is preferably more resistant to fungal infection relative to a non-transgenic plant of the same species.

Compositions Containing Antifungal Proteins

The antifungal proteins of the present invention may also be provided in a composition suitable for application to plants. General methods of preparing the compositions have been described (Martens, 1979; Winnacker-Kuchler, 1986). The composition generally comprises an antifungal ribosomal protein with a small molecular weight and a high pI. The pI of such a protein preferably is greater than about 7, more preferably is greater than about 10, and most preferably is greater than about 11.5. The molecular weight preferably is between about 2 kDa and about 20 kDa, more preferably is between about 2 kDa and about 15 kDa, and most preferably is between about 3 kDa and about 7 kDa.

The antifungal protein preferably is at least about 85% identical to SEQ ID NO:1, more preferably is at least about 86%, 87%, 88%, 89%, 90%, 91%, 92%, 93%, 94%, 95%, 96%, 97%, 98%, or 99% identical to SEQ ID NO:1, and most preferably is SEQ ID NO:1.

The antifungal protein in the composition, comprising an amino acid sequence at least between about 85% and about 100% identical with SEQ ID NO:1, is preferably reactive with an antibody raised against an antigenic epitope from SEQ ID NO:1.

The antifungal protein may also preferably be at least about 85% identical to SEQ ID NOS: 19, 20, 21, 22, 23, 24, 31, 32, 33, 34, or 35, more preferably at least about 86%, 87%, 88%, 89%, 90%, 91%, 92%, 93%, 94%, 95%, 96%, 97%, 98%, or 99% identical to SEQ ID NOS: 19, 20, 21, 22, 23, 24, 31, 32, 33, 34, or 35, and most preferably SEQ ID NOS: 19, 20, 21, 22, 23, 24, 31, 32, 33, 34, or 35.

The antifungal protein may also be used in combination with other antifungal agents, so as to provide a broader spectrum of activity. Examples of such other antifungal agents include *Bacillus thuringiensis* endotoxin, chitinases, cysteine-rich chitin-binding proteins, β-1,3-glucanases, permatins (including zeamatins), defensins, thionins, ribosome-inactivating proteins, and non-specific lipid transfer proteins. The antifungal protein may also be used in combination with various chemical antifungal agents including polyoxines, nikkomycines, carboxyamides, aromatic carbohydrates, carboxines, morpholines, inhibitors of sterol biosynthesis, and organophosphorus compounds (Worthington and Walker, 1983).

The composition may also contain other types of antimicrobial agents including antibiotics, insecticides, acaricides, nematicides, herbicides, or other such compounds. The composition may further comprise carrier molecules, surfactants, fertilizers, growth regulators, solvents, inert materials, attractants, sterilizing agents, or equivalent types of additives. The use of many of these additives in compositions has been described (Watkins, 1955; Winnacker-Kuchler, 1986).

Alternatively, the antifungal protein may be expressed by transformed host cells that colonize a host plant. For instance, a bacteria or yeast cell may be transformed with a nucleic acid encoding an antifungal protein (as described above) and allowed to colonize on a host plant. As a colony of these transformed host cells is established, the cells in the colony typically produce the antifungal protein. This affords the host plant a degree of protection against fungal infections.

The antifungal protein, whether provided in a transgenic plant, a transformed host cell, or a composition, may have antifungal activity against a broad range of genera and species including: *Alternaria* (*Alternaria brassicola; Alternaria solani*); *Ascochyta* (*Ascochyta pisi*); *Botrytis* (*Botrytis cinerea*); *Cercospora* (*Cercospora kikuchii; Cercospora zaea-maydis*); *Colletotrichum* (*Colletotrichum lindemuthianum*); *Diplodia* (*Diplodia maydis*); *Erysiphe* (*Erysiphe graminis* f. sp. *graminis; Erysiphe graminis* f. sp. *hordei*); *Fusarium* (*Fusarium nivale; Fusarium oxysporum; Fusarium graminearum; Fusarium culmorum; Fusarium solani; Fusarium moniliforme; Fusarium roseum*); *Gaeumanomyces* (*Gaeumanomyces graminis* f. sp. *tritici*); *Helminthosporium* (*Helminthosporium turcicum; Helminthosporium carbonum; Helminthosporium maydis*); *Macrophomina* (*Macrophomina phaseolina; Maganaporthe grisea*); *Mycosphaerella* (*Mycosphaerella figiensis*); *Nectria* (*Nectria heamatococca*); *Peronospora* (*Peronospora manshurica; Peronospora tabacina*); *Phoma* (*Phoma betae*); *Phymatotrichum* (*Phymatotrichum omnivorum*); *Phytophthora* (*Phytophthora cinnamomi; Phytophthora cactorum; Phytophthora phaseoli; Phytophthora parasitica; Phytophthora citrophthora; Phytophthora megasperma* f. sp. *sojae; Phytophthora infestans*); *Plasmopara* (*Plasmopara viticola*); *Podosphaera* (*Podosphaera leucotricha*); *Puccinia* (*Puccinia sorghi; Puccinia striiformis; Puccinia graminis* f. sp. *tritici; Puccinia asparagi; Puccinia recondita; Puccinia arachidis*); *Puthium* (*Puthium aphanidermatum*); *Pyrenophora* (*Pyrenophora tritici-repentens*); *Pyricularia* (*Pyricularia oryzae*); *Pythium* (*Pythium ultimum*); *Rhizoctonia* (*Rhizoctonia solani; Rhizoctonia cerealis*); *Scerotium* (*Scerotium rolfsii*); *Sclerotinia* (*Sclerotinia sclerotiorum*); *Septoria*(*Septoria lycopersici; Septoria glycines; Stagonospora nodorum/Phaeosphaeria nodorum; Septoria tritici*); *Thielaviopsis* (*Thielaviopsis basicola*); *Uncinula* (*Uncinula necator*); *Venturia* (*Venturia inaequalis*); or *Verticillium* (*Verticillium dahliae; Verticillium albo-atrum*). Most preferably, the antifungal proteins of the present invention display activity against *Botrysis, Cercospora, Erysiphe, Fusarium, Phytophthora, Puccinia, Rhizoctonia, Sclerotinia, Septoria*, or *Verticillium*.

Method for Preparing Transformed Host Cells Containing an Antifungal Protein

The invention is further directed to a method for preparing a transformed host cell comprising, in a 5' to 3' orientation: a promoter to direct the transcription of a structural nucleic acid sequence, a structural nucleic acid sequence, a 3' transcriptional terminator, and a 3' polyadenylation signal.

The method generally comprises the steps of selecting a suitable host cell, transforming the host cell with a recombinant vector, and obtaining the transformed host cell. There are many methods for introducing nucleic acids into host cells. Suitable methods include bacterial infection (e.g., *Agrobacterium*), binary bacterial artificial chromosome vectors, direct delivery of DNA (e.g., via PEG-mediated transformation, desiccation/inhibition-mediated DNA uptake, electroporation, agitation with silicon carbide fibers, and acceleration of DNA coated particles, etcetera (reviewed in Potrykus et al., 1991).

Technology for introduction of DNA into cells is well known to those of skill in the art. These methods can generally be classified into four categories: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253), and particle acceleration (Johnston and Tang, 1994; Fynan et al., 1993); (3) viral vectors (Clapp, 1993; Lu et al., 1993; Eglitis and Anderson, 1988); and (4) receptor-mediated mechanisms (Curiel et al., 1992; Wagner et al., 1992).

Alternatively, nucleic acids can be introduced into pollen by directly injecting a plant's reproductive organs (Zhou et al., 1983; Hess, 1987; Luo et al., 1988; Pena et al., 1987). The nucleic acids may also be injected into immature embryos (Neuhaus et al., 1987).

The recombinant vector used to transform the host cell typically comprises, in a 5' to 3' orientation: a promoter to direct the transcription of a structural nucleic acid sequence, a structural nucleic acid sequence, a 3' transcriptional terminator, and a 3' polyadenylation signal. The recombinant vector will preferably comprise a promoter selected for its desired expression characteristics, the nucleic acid sequence of the present invention as previously described, and a suitable 3' terminator and polyadenylation signal. The recombinant vector may further comprise untranslated sequences, transit and targeting sequences, selectable markers, enhancers, or operators.

Method for Preparing Transgenic Plants Containing an Antifungal Protein

The invention is further directed to a method for preparing transgenic plants more resistant to fungal infections than non-transgenic plants of the same species, comprising selecting a suitable plant cell, transforming the plant cell with a recombinant vector, obtaining the transformed host cell, and regenerating a transgenic plant.

The recombinant vector typically comprises, in a 5' to 3' orientation: a promoter to direct the transcription of a structural nucleic acid sequence, a structural nucleic acid sequence, a 3' transcriptional terminator, and a 3' polyadenylation signal. The recombinant vector may further comprise untranslated sequences, transit and targeting sequences, selectable markers, enhancers, or operators.

The regeneration, development, and cultivation of plants from transformed plant protoplast or explants is well taught in the art (Weissbach and Weissbach, 1988; Horsch et al., 1985). In this method, transformants are generally cultured in the presence of a medium that selects for the successfully transformed cells and induces the regeneration of plant shoots (Fraley et al., 1983). These shoots are typically obtained within two to four months.

The shoots are then transferred to an appropriate root-inducing medium containing the selective agent and an antibiotic to prevent bacterial growth. Many of the shoots will develop roots. These are then transplanted to soil or other media to allow the continued development of roots. The method, as outlined, will generally vary depending on the particular plant strain employed.

Preferably, the regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transgenic plant may pass along the nucleic acid sequence encoding the antifungal protein to its progeny. The transgenic plant is preferably homozygous for the nucleic acid encoding the antifungal protein and transmits that sequence to all of its offspring as a result of sexual reproduction. Progeny may be grown from seeds produced by the transgenic plant. These additional plants may then be self-pollinated to generate a true breeding line of plants.

The progeny from these plants are evaluated, among other things, for gene expression and disease resistance (e.g., antifungal properties). The gene expression may be detected by several common methods such as western blotting, northern blotting, immunoprecipitation, and ELISA. Disease resistance is generally tested in the field under a range of environmental conditions.

The transgenic plant may generally be any type of plant, preferably is one with agronomic, horticultural, ornamental, economic, or commercial value, and more preferably is an *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, or zucchini plant.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Isolation of an Antifungal Protein

*Fusarium culmorum* from a stock culture was used to inoculate petri plates containing solid synthetic medium. The solid synthetic medium (Terras et al., 1993) contained $K_2HPO_4$ (2.5 mM), $MgSO_4$ (50 μM), $CaCl_2$ (50 μM), $FeSO_4$ (5 μM), $CoCl_2$ (0.1 μM), $CuSO_4$ (0.1 μM), $Na_2MoO_4$ (2 μM), $H_3BO_3$ (0.5 μM), KI (0.1 μM), $ZnSO_4$ (0.5 μM), $MnSO_4$ (0.1 μM), glucose (10 μL), asparagine (1 g/L), methionine (20 mg/L), myo-inositol (2 mg/L), biotin (0.2 mg/L), thiamine-HCl (1 mg/L), pyridoxine-HCl (0.2 mg/L), and Bacto-agar (Difco, Detroit, Mich., 15 g/L). The plates were incubated at 22° C. for about 1 week. Sporulation was then induced by cutting the fungus into cross sectional pieces in the petri plate using a spatula. After several days, the plates were scraped and the spores harvested.

Flasks containing liquid synthetic media (same media as above without the agar) were inoculated with the harvested spores. After overnight incubation at 22° C. with gentle stirring, new fungal spores were produced and collected by filtration. These spores were washed with 20 mM sodium acetate (pH 5.2), and then washed with 20 mM sodium acetate (pH 3.2) containing 1 M NaCl to release proteins off fungal cells. The high salt wash was then precipitated with ammonium sulfate at 80% saturation. The precipitate was collected, redissolved in 20 mL distilled $H_2O$, and dialyzed against distilled water (3 changes of water over 24 hours). The dialyzed spore solution was dried to completion in a Savant SPEEDVAC AES 2000 (SPEEDVAC is a registered trademark of Savant Instruments, Inc., Holbrook, N.Y.) and redissolved in 200 μL distilled water.

The spore solution was then passed through a SUPEROSE-12 FPLC gel filtration column (SUPEROSE is a registered trademark of Pharmacia Inc., Piscataway, N.J.). Spore proteins were eluted in phosphate buffered saline at a flow rate of 0.4 mL/minute. Fractions containing proteins were detected by UV absorbance at 280 nm.

Fractions were tested for antifungal activity against *Fusarium culmorum* (as described in Example 4). The fractions that exhibited fungicidal activity were collected and loaded onto a MONO Q anion exchange column (MONO Q is a registered trademark of Pharmacia Inc., Piscataway, N.J.). The column was then washed several times with 50 mM Tris, pH 9.0 (solution A). Proteins were eluted from the column by gradually increasing the amount of solution B (50 mM Tris, pH 9.0, and 1 M NaCl) passing through the column, relative to solution A. A linear gradient was used in which solution B increased from 0% to 40% at a rate of 1% each minute.

Fractions containing proteins eluted from the MONO Q column were independently collected and loaded onto an analytical C18 reverse phase chromatography column (VYDAC, Hesperia, Calif.). The column was washed several times using solvent A (0.1% trifluoroacetic acid in water). Proteins were eluted in a linear gradient in which solvent B (0.1% trifluoroacetic acid in acetonitrile) was increased at a rate of 1% B each minute while the flow rate was 1 mL/minute. Proteins were detected by UV light absorbance at a wavelength of 214 nm.

Each fraction collected was again tested for antifungal activity (as described in Example 4) Fractions exhibiting antifungal activity were dried to completion in the SPEED-VAC and redissolved in 50 µL distilled water.

Example 2

Characterization of the Antifungal Protein

Gel electrophoresis was employed to detect proteins contained in the fractions exhibiting antifungal activity (Laemmli, 1970). Briefly, a sample from the fraction was dissolved in denaturing sample buffer (450 mM Tris-HCl, pH 8.45, 12% (v/v) glycerol, 4% (w/v) SDS, 0.06% (w/v) Coomassie Blue G, and 0.0025% (w/v) Phenol Red) and boiled for 10 minutes. The sample was then loaded onto a 16% tricine gel and electrophoresed in electrophoresis buffer (100 mM Tris, 100 mM tricine, and 1% SDS) at 125V for two hours. The buffers and gel were obtained from Novex Co., San Diego, Calif.

Silver staining (Integrated Separation Systems, Natick, Mass.) revealed a protein of approximately 95% purity with a molecular weight of approximately 5 kDa.

Example 3

Sequencing the Purified Antifungal Protein

In order to determine the amino acid sequence of the protein in the antifungal fraction, the purified protein from Example 1 was denatured in 8 M urea containing 8 mM dithiothreitol. These denaturing reagents were then removed by dialysis against distilled water using a membrane having a molecular weight cut off of 1,000 (Spectra/PorO, Spectrum, Houston, Tex.).

Automated Edman degradation was carried out on an Applied Biosystems Model 470A Protein Sequenator (Applied Biosystems, Norwalk, Conn.), using conditions recommended by the manufacturer. The PTH-amino acid derivatives were identified by reversed phase analysis in an on-line fashion employing an Applied Biosystems Model 120 PTH Analyzer.

N-terminal sequencing of the protein resolved a full-length amino acid sequence of SEQ ID NO:1. The sequence consists of 40 amino acids, 40% of which are basic. Sequence database searches in GenBank revealed that the sequence had not previously been identified. This novel protein was assigned the name FCWP1.

Example 4

Testing the Antifungal Activity of FCWP1

The fungicidal activity of FCWP1 was determined against several fungal species in an in vitro antifungal assay. The assay was performed in sterile 96-well flat-bottom microtiter plates.

*Fusarium culmorum* spores were obtained as described in Example 1 and resuspended in double strength testing media ($K_2HPO_4$ (5 mM), $MgSO_4$ (100 µM), $CaCl_2$ (100 µM), $FeSO_4$ (10 µM), $CoCl_2$ (0.2 µM), $CuSO_4$ (0.2 µM), $Na_2MoO_4$ (4 µM), $H_3BO_3$ (1.0 µM), KI (0.2 µM), $ZnSO_4$ (1.0 µM), $MnSO_4$ (1.0 µM), glucose (20 g/L), asparagine (2 g/L), methionine (40 mg/L), myo-inositol (4 mg/L), biotin (0.4 mg/L), thiamine-HCl (2 mg/L), pyridoxine-HCl (0.4 mg/L)) at a concentration of $2 \times 10^4$ spores/mL. Approximately 1000 spores were added (50 µl) to each test well. These spores were allowed to germinate for 5 to 15 hours at 22° C.

*Phytophthora infestans* spores were obtained from LB-V-8 agar plates (5.5 oz. of V-8 juice, 23 grams of Lima Bean agar (Difco, Detroit, Mich.), and 2.3 grams of $CaCO_3$) that were inoculated with a 5 mm section of fungal mycelium from a stock culture. These plates were incubated for about ten days at 18° C. Sporulation was induced by macerating the fungal growth with a sterile glass rod. Approximately five days later, the sporangia were collected by washing the surface of the assay plate with 15% V-8 liquid medium (5.5 oz. of V-8 juice mixed with solid $NaHCO_3$ until the pH is approximately 6.0), centrifuged at 15,000×g for 30 minutes, filter-sterilized using a 0.22 micron filter, and diluted to 15% with sterile distilled water. About 1000 sporangia were added per well in a total volume of 50 µL. These spores were allowed to germinate for 5 to 15 hours at 18° C.

After spore germination, 50 µL of sterile solution containing the test protein in distilled water were added to each of the test wells. The FCWP1 protein was tested in a concentration range from 0 to 80 µg/mL to determine $IC_{50}$ values. Protein concentrations were determined using the BCA protein assay kit obtained from Pierce Co. (Rockford, Ill.).

The assay was performed under low and high salt conditions. To test wells designated for high salt conditions, $CaCl_2$ and KCl were added to final concentrations of 1 mM and 50 mM, respectively. This salt-supplemented medium is referred to as "high salt medium." The low salt conditions were provided by the media in which the spores were resuspended without additional supplements. This medium is referred to as "low salt medium."

The spores were incubated with the test proteins under the low or high salt conditions for 15 to 24 hours at 24° C.

Table 2 shows the antifungal activity of FCWP1 against *Fusarium culmorum*, the causal agent of wheat head scab, and *Phytophthora infestans*, the causal agent of late blight in potato and tomato. The antifungal activity is expressed as the concentration in µg/mL required to cause 50% inhibition of fungal hyphal growth ($IC_{50}$). The percentage of fungal hyphal growth inhibition is defined as $$\frac{\text{average hyphae length in a test culture}}{\text{average hyphae length in a control culture}} \times 100$$

The test culture was treated with a solution of water containing the antifungal protein. The control culture was treated with water only.

TABLE 2

Antifungal Activity of Purified FCWP1

| Fungus | $IC_{50}$ (µg/mL) | |
|---|---|---|
| | Low salt | High salt |
| F. culmorum | 5 | >50 |
| P. infestans | 5 | 20 |

The data in Table 2 demonstrate that FCWP1 exhibits potent antifungal activity against *Fusarium* and *Phytophthora*, which cause disease on many crop plants. The concentration in µg/mL required to cause 50% inhibition of fungal hyphal growth ($IC_{50}$) can be realistically achieved in plants transformed with a nucleic acid sequence encoding the FCWP1 protein.

Example 5

Production of a Synthetic FCWP1 Protein

A synthetic protein identical to that of SEQ ID NO:1 was produced by Bio•Synthesis Inc. (Lewisville, Tex.). The purity of the synthetic FCWP1 was determined by mass spectral analysis to be >95%. The molecular weight of the synthetic FCWP1 was 4,504 Daltons, as determined by mass spectral analysis.

This synthetic FCWP1 protein was tested in an in vitro fungal assay against *F. culmorum*, *P. infestans*, and *S. nodorum*. The assay was performed as described in Example 4. These results (Table 3) demonstrate that the antifungal activity of the synthetic FCWP1 protein is essentially the same as that of the native FCWP1 purified from *F. culmorum* (Table 2).

TABLE 3

Antifungal Activity of a Synthetic FCWP1 Protein

| Fungi | $IC_{50}$ (µg/mL) | |
|---|---|---|
| | Low salt | High salt |
| *F. culmorum* | 6 | 85 |
| *S. nodorum* | 22 | >170 |
| *P. infestans* | 10 | 20 |

Example 6

Production of a Nucleic Acid Sequence Encoding the FCWP Protein

The FCWP1 antifungal protein consists of 40 amino acids. Using the amino acid sequence of SEQ ID NO:1, a nucleic acid molecule encoding FCWP1 was constructed by PCR. All of the reactions described (3' extension of the annealed PCR products and the PCR amplification of the full length sequence) were conducted in a single tube, in a single PCR reaction using the Long Range Template PCR kit (Boehringer Mannheim Corp., Indianapolis, Ind.) following the conditions suggested by the manufacturer. The kit included all the necessary enzymes and buffers. Oligonucleotide primers were produced by Midland Certified Reagent Co., (Midland, Tex.).

Regulatory elements, such as an initiating methionine (ATG) codon and a stop codon, were added to the nucleic acid sequence. Due to the degeneracy of the genetic code, several codons are possible for any particular amino acid. Each type of cell or organism, however, has a preferred pattern of codon usage. The codon usage was selected such that it was optimal for several different systems including *E. coli*, yeast, and potato. Optimal codon usage was determined as described by Campbell et al. (1990).

The full length synthetic fcwp1 was produced using PCR in a two-step reaction. First, a double-stranded nucleic acid molecule was produced that contained the coding sequence of fcwp1. An oligonucleotide primer (SEQ ID NO:3) consisting of the first 75 nucleotides of the fcwp1 sense strand was annealed to a second oligonucleotide primer (SEQ ID NO:4) consisting of 77 nucleotides of the fcwp1 antisense strand. These two oligonucleotides are complementary to each other over a region of 25 base pairs. A double-stranded DNA molecule encoding the full length FCWP1 protein was obtained by PCR reaction followed by 3'-extension of the annealed products.

In a second reaction, this double-stranded fcwp1 DNA was amplified. This was accomplished by using two primers (SEQ ID NOS:5 and 6) that anneal to the 3' end of the fcwp1 sense and antisense strands, respectively. The amplifying primers contained restriction sites for BamHI and NcoI (SEQ ID NO:5), and EcoRI (SEQ ID NO:6). These provide convenient sites for subcloning the final PCR product.

The final PCR product was separated on a 2% agarose gel, and a nucleic acid band of about 140 base pairs was visualized after ethidium bromide staining. This nucleic acid band was purified from the gel and ligated into plasmid pNoTA/T7 (Invitrogen, San Diego, Calif.).

The sequence of the synthetic gene was confirmed using a 373 DNA Sequencer Stretch Model from Applied Biosystem using the PRISM Ready Reaction Dideoxy Terminator Cycle Sequencing Kit following the manufacturer's instructions (Applied Biosystems, Inc., Foster City, Calif.).

Example 7

Construction of Recombinant Vectors for Transformation

The fcwp1 synthetic nucleic acid sequence (SEQ ID NO:2) was fused in a PCR reaction to a second nucleic acid sequence (SEQ ID NO:8) encoding a signal peptide from the AlyAFP protein. The signal sequence is described in U.S. Pat. No. 5,773,696. Immunohistochemical studies indicated that this signal peptide functions to target the protein to the extracellular space of plant tissue.

In all PCR reactions described, the Long Range Template PCR kit (Boehringer Mannheim, Indianapolis, Ind.) was used, following the conditions suggested by the manufacturer. Oligonucleotide primers were produced by Midland Certified Reagent Co. (Midland, Tex.).

In the first PCR reaction, a fusion between the AlyAFP signal sequence and fcwp1 was constructed. The two primers used for amplification were (1) a 38-mer (SEQ ID NO:7) with 14 nucleotides that provided restriction sites and 24 nucleotides complementary to the 5' terminus of the AlyAFP signal sequence; and (2) a 41-mer (SEQ ID NO:8) with 10 nucleotides corresponding to the C-terminus of the AlyAFP signal sequence and 31 nucleotides complementary to the 5' end of fcwp1 (including an ATG start site). Plasmid pMON22652 (FIG. 1) was used as a template for the PCR reaction. The PCR product was separated on an agarose gel and observed as a 130 base pair fragment after staining with ethidium bromide. The fragment was excised from the agarose gel and purified using an ULTRAFREE-MC centrifugation filtration unit (ULTRAFREE is a registered trademark of Millipore Inc., Bedford, Mass.).

A second PCR reaction used the plasmid containing the fcwp1 synthetic nucleic acid sequence of SEQ ID NO:2 as a template for producing a full-length fcwp1 template. The two primers used for amplification were (1) a 20-mer (SEQ ID NO:9) containing the 5' portion of the fcwp1 synthetic gene; and (2) a 30-mer (SEQ ID NO:10) containing 21 nucleotides complementary to the 3' terminus of the fcwp1 nucleic acid sequence along with 9 nucleotides for a BamHI cloning site. The PCR product, a 150 base pair fragment, was purified from a gel as described previously.

A third PCR reaction generated the final full-length AlyAFP signal sequence/fcwp1 fusion product of approximately 250 base pairs (SEQ ID NO:11). This nucleic acid molecule was gel purified and used for subsequent cloning steps.

The BamHI restriction sites located on the 5' and 3' ends of the fusion product were utilized to clone the final AlyAFP signal sequence/fcwp1 fusion product into a previously constructed FMV expression cassette vector, pMON1770.

Figure 2:
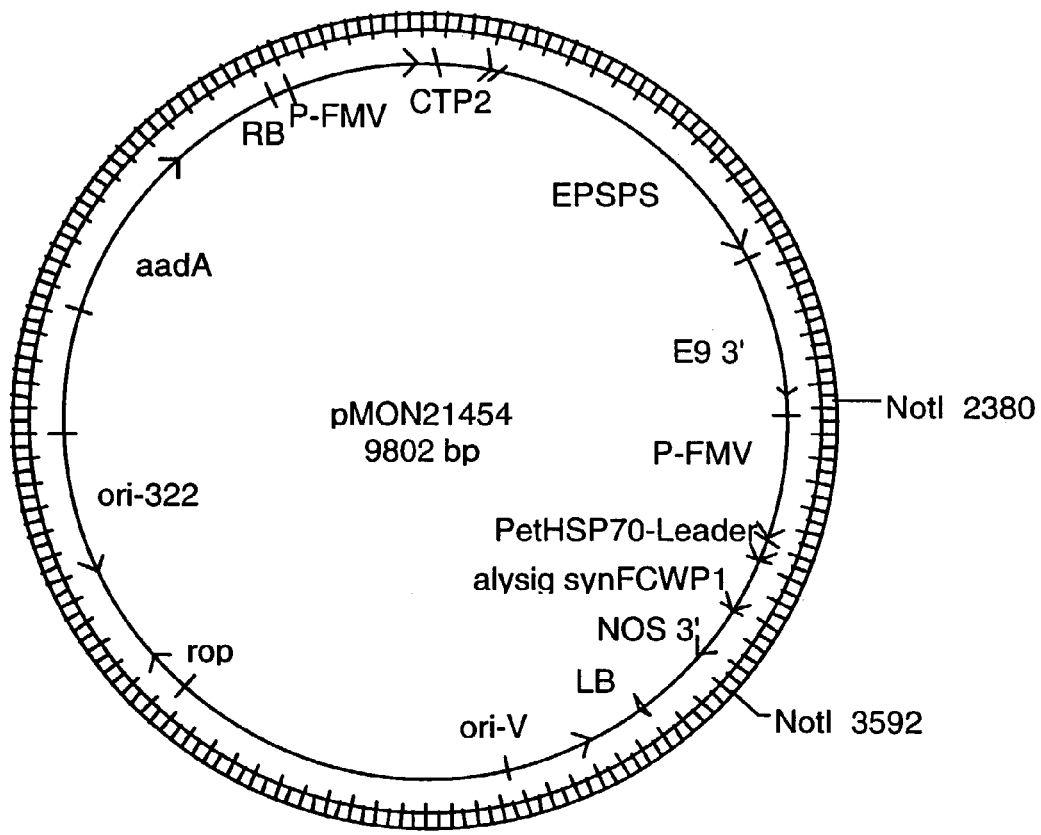
FIG. 2 is a plasmid map of pMON21454.
Figure 5:
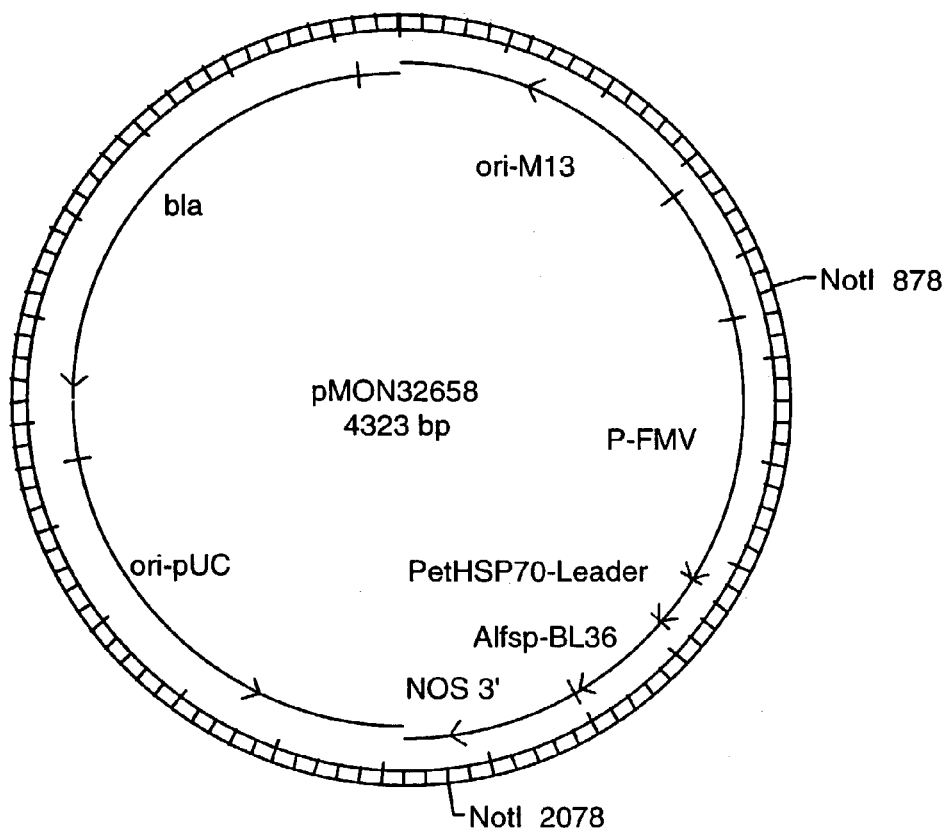
FIG. 5 is a plasmid map of pMON32658.

After cloning the fusion sequence into pMON11770, the vector was digested with restriction enzyme NotI. This liberated a fragment containing the entire expression cassette (i.e., 5'FMV promoter, Hsp70 leader sequence, AlyAFP signal sequence/fcwp1 fusion, and nos3'). This expression cassette was then inserted into the double border plant transformation vector pMON17227. The resulting plasmid was designated pMON21454 (FIG. 2).

The pMON21454 vector contains the following sequence elements linked in the 5' to 3' direction: an FMV promoter; Spc/Str, conferring resistance to spectinomycin and streptomycin; the right border region of the T-DNA; 5-enolpyruvyl-3-phoshoshikimate synthase (EPSPS) sequence, conferring resistance to glyphosate; the E9 3' sequence, a transcriptional termination site and polyadenylation signal sequence; an FMV promoter; the Hsp70 leader sequence; the AlyAFP signal/fcwp1 fusion; the nos 3' sequence; the left border of the T-DNA; and the origin of replication (ori-322).

Example 8

Purification of mRNA

Total cellular RNA was harvested from partially lyophilized *Fusarium culmorum* germinated spores using the TRIZOL Reagent kit (TRIZOL is a registered trademark of GIBCO BRL/Life Technologies, Inc., Gaithersburg, Md.), according to the manufacturer's protocol. The harvested RNA was further purified using oligo(dT) cellulose (GIBCO BRL/Life Technologies, Gaithersburg, Md.) as described by Celano et al. (1993).

Example 9

Synthesis of the First Strand of cDNA

The purified poly-A RNA from Example 8 was used as a template for reverse transcription PCR (RT-PCR) using a poly-A oligonucleotide primer. This reverse transcription reaction was performed using the 5' RACE Kit (GIBCO BRL/Life Technologies, Gaithersburg, Md.), according to the manufacturer's instructions. The reaction yielded a first strand of the cDNA. After removal of the mRNA strand by RNase H1 digestion and spin cartridge separation, a poly-C tail was added to the single-stranded fcwp1 cDNA using a terminal deoxynucleotide transferase under conditions recommended by the enzyme manufacturer. The 5' region of the gene was amplified by PCR using the GeneAmp DNA Amplification Reagent Kit (Perkin Elmer Cetus) and the reaction conditions recommended by the manufacturer.

Example 10

Amplification and Sequencing of the 5' End of the cDNA

The first strand of the fcwp1 cDNA was used in a PCR reaction to produce a double-stranded cDNA. The two primers used for amplification were (1) a mixed oligonucleotide 34-mer (SEQ ID NO:12) with 14 nucleotides providing restriction sites and 20 nucleotides complementary to the 3' end of the fcwp1 cDNA strand, and (2) an oligo-dG primer (SEQ ID NO:13) that anneals to the poly-C tail of the fcwp1 cDNA strand.

PCR reaction products were analyzed by agarose gel electrophoresis, and a single nucleic acid band of about 480 base pairs was present in the complete reaction mixture, but not in the control reaction mixture that contained only one primer. This band was cut out of the gel, and the DNA was isolated using an Ultrafree-MC centrifugation filter unit (Millipore, Bedford, Mass.). The DNA fragment was digested with BamH1 and cloned into the plasmid pGEM11Zf (+) (Promega, Madison, Wis.).

The inserted fcwp1 5' cDNA was sequenced on a Applied Biosystems 373 DNA Sequencer Stretch Model using the PRISM Ready Reaction Dideoxy Terminator Cycle Sequencing Kit (Applied Biosystems, Inc., Foster City, Calif.). The 5' fcwp1 cDNA sequence is shown in SEQ ID NO:14.

Example 11

Amplification and Sequencing of the 3' End of the cDNA

The 3' region of the fcwp1 cDNA was cloned as follows: First strand cDNA generated for 5' RACE was used as template for the amplification of the 3' portion of the fcwp1 cDNA strand by PCR using the GeneAmp DNA Amplification Reagent Kit (Perkin Elmer Cetus, Norwalk, Conn.). The reaction was performed according to the manufacturer's instructions.

The two primers used for amplification were (1) an oligonucleotide 37-mer (SEQ ID NO:15) with 14 nucleotides for cloning sites and 23 nucleotides complementary to positions 268 to 288 of the 5' fcwp1 cDNA sequence; and (2) an oligo-dT primer (SEQ ID NO:16) that anneals to the poly(A) tail of the fcwp1 cDNA. PCR reaction products were analyzed by agarose gel electrophoresis. A single nucleic acid band of about 550 base pairs was present in the complete reaction mixture, but not in the control reaction mixture containing only one primer. This band was cut out of the gel, and the DNA was isolated using an Ultrafree-MC centrifugation filter unit (Millipore, Bedford, Mass.). The DNA fragment was digested with BamHI, cloned into the plasmid pGEM11Zf (+) (Promega), and sequenced as described previously. The 3' fcwp1 sequence is shown in SEQ ID NO:17.

Example 12

Amplification of the Full Length cDNA

The 5' region (SEQ ID NO:14) and the 3' region (SEQ ID NO:17) of fcwp1 cDNA overlapped by 193 nucleotides. A full-length fcwp1 cDNA, as shown in SEQ ID NO:18, was formed by combining nucleotides 1 to 454 of SEQ ID NO:14 with nucleotides from position 202 to the end of SEQ ID NO:17 in a PCR reaction as described previously.

As shown in FIG. 3, the fcwp1 cDNA contains a 90-base-pair 5' leader sequence, a 408-base-pair open reading frame coding for a 136-amino-acid protein, and a 3' untranslated region of 213 base pairs leading up to the poly(A) tail.

The fcwp1 cDNA is capable of encoding a protein of up to 136 total amino acids. Amino acids 95-136 comprise the FCWP1 protein of SEQ ID NO:1.

Example 13

Identification of Related Sequences

The Gen EMBL database was searched using FastA with the BLOSUM 50 scoring matrix on GCG software (Genetics Computer Group, Inc., Madison, Wis.) in order to identify any sequences closely related to FCWP1 or fcwp1. The sequence sharing the greatest sequence identity with FCWP1 was the ribosomal protein RPG19, isolated from *Rhizomucor racemosus* (Sosa et al., 1989). The amino acid sequence of FCWP1 was aligned with the amino acid sequence of RPG19 (FIG. 4). The FCWP1 protein is underlined. The two proteins display 58% identity.

Example 14

Detection of Purified FCWP1

Purified FCWP1 was spiked into boiled Russet Burbank crude leaf extracts and into boiled potato leaf intercellular wash fluid (pIWF). Protein extracts from the leaves were then prepared in a grinding buffer (20% (w/v) SDS, 10% (v/v) glycerol, 0.125 M Tris, pH 8.45) and analyzed by SDS polyacrylamide gel electrophoresis (SDS PAGE). Tricine gels (Novex, San Diego, Calif.) were used to enhance separation of low molecular weight proteins. After electrophoresis, the proteins were electrophoretically transferred to IMMOBILON-P PVDF microporous membrane (IMMOBILON is a registered trademark of Millipore, Bedford, Mass.). Following transfer, the membranes were blocked with 5% (w/v) dry milk in TBST (10 mM Tris, 0.15 M NaCl, 0.05% (v/v) Tween-20, at pH 8.0).

After blocking, the membrane was probed with anti-FCWP1 polyclonal antibody. The rabbit polyclonal antibodies against FCWP1 protein were prepared by Pocono Rabbit Farm (Canadensis, Pa.). The antibody had been preadsorbed to crude Russet Burbank leaf tissue extract to reduce non-specific binding of the antibody to proteins normally found in potato leaf tissue. After several washes, the membrane was incubated with a secondary anti-rabbit antibody labeled with horseradish peroxidase (Amersham Corp., Arlington Heights, Ill.). Detection of the antibody specific bands was accomplished using an enhanced chemiluminescence procedure in which light-emitting bands are visualized by exposure of the membrane to film (ECL Western Blotting kit, Amersham, Arlington Heights, Ill.). The size of the FCWP1 protein was estimated to be 5 kDa.

Example 15

Isolation of Potato Intercellular Wash Fluid

Potato intercellular wash fluid (pIWF) was isolated from eight freshly harvested Russet Burbank potato leaves. Medium-sized leaves were cut from the plants near the base of the leaf and were immediately placed in distilled, deionized water. The leaves were transferred to a 1 L vacuum flask containing approximately 350 mL distilled, deionized water. A vacuum was applied to the flask for 10-15 seconds to remove air from the intercellular spaces. The vacuum was then quickly released to promote saturation of the intercellular spaces with water. This infiltration was repeated 3-4 times. The leaves were removed from the water and blotted dry. The leaves were then rolled and placed into a syringe. Intercellular wash fluid was harvested by centrifugation at about 300×g. The wash fluid was then cleared of any dark green pigment by centrifugation at 16,000×g for 10 minutes in a tabletop microfuge. The pIWF was then stored on ice until use.

Example 16

Determination of FCWP1 Proteolysis Sites

The FCWP1 proteolysis sites were determined by mass spectrometry. Freshly isolated pIWF was diluted 1:5 with 50 mM MES buffer pH 6.0 (Sigma Co., St. Louis, Mo.), to yield a final protein concentration of 114 µg/mL. FCWP1 was diluted in 50 mM MES, pH 6.0 to give a final protein concentration of 200 µg/mL. To initiate proteolysis, 5 µL of FCWP protein was added to 5 µL of pIWF. Proteolysis was allowed to proceed for 0.5, 0.75, 1, 2, and 5 minutes. The proteolysis was terminated by placing the sample in a boiling water bath for 4 minutes. The samples were frozen in dry ice and stored until analysis by MALDI-TOF (matrix-assisted laser desorption/ionization time-of-flight) mass spectrometry to compare the pattern of molecular weights of the proteolytic fragments with that of the parent protein.

For analysis, the protein samples were diluted 1:10 into a matrix solution comprising 10 mg/mL α-cyano-4-hydroxycinnamic acid dissolved in 60% acetonitrile, 20% methanol, 0.3% trifluoroacetic acid, and 20% water. An aliquot (1 µL) was spotted on a sample plate for analysis. Control samples included pIWF without added protein, and boiled (denatured) pIWF with protein.

Proteolytic analysis of FCWP did not reveal any obvious sequence-dependent cleavage sites. To aid in the identification of proteolytic consensus sites, other ribosomal protein sequences were analyzed. These included YL46 (SEQ ID NO:34), SL23 (SEQ ID NO:33), and BL32 (SEQ ID NO:31). Analysis was performed as described above. The sequences were then converted from the 20 amino acid code into a code that groups amino acids together based on common physical properties (amino acid abbreviations correspond to the single letter code). The code for each amino acid is as follows:

Polar (G, S, T, C, N, Q, P, H)=1
Hydrophobic (A, V, L, I, M, F, W, Y)=0
Basic (K, L)=(+)
Acidic (E, D)=(−)

The FCWP and ribosomal protein sequences were converted from the 20 amino acid code to a 4 "letter" code using the guide above. From this code, a "loose" consensus appeared for approximately half of the sites: . . . 1 0*(+/1)*1 1 . . . (in which the symbol * indicates a proteolytic site). Every occurrence of this pattern resulted in hydrolysis at both cut sites.

Example 17

Construction of FCWP1 Variants

A number of variants that contained altered proteolytic sites were synthetically produced (SEQ ID NOS:19-24). The protein sequences and proteolytic sites of the parent protein (FCWP1) and the variants are shown in Table 4. FCWP1 is the wild-type protein. Mutated residues are indicated by text in bold. A * indicates a site of proteolysis.

TABLE 4

Various FCWP Proteins

| Protein (SEQ ID NO) | Sequence |
| --- | --- |
| FCWP1 (1) | VKVGLA*TKAERASRQQRKQRKNRQKTL*R*GTA*KVKGAKAKK |
| FCWP2 (19) | VKVGLA*TKAERASRQQRKQRKNRQKTL*M*GTA*KVKGAKAKK |
| FCWP3 (20) | VKVGLA*TKAERASRQQRKQRKNRQKTR*RG*TA*KVKGAKAKK |

TABLE 4-continued

Various FCWP Proteins

| Protein (SEQ ID NO) | Sequence |
|---|---|
| FCWP4 (21) | VKVGLA*TKAERASRQQRKQRKNRQKTL*R*GTA*QVKGAKAKK |
| FCWP5 (22) | VKVGLA*TKAERASRQQRKQRKNRQKTL*R*GTR*KVKGAKAKK |
| FCWP6 (23) | VKVGLA*TKAERASRQQRKQRKNRQKTL*M*GTA*QVKGAKAKK |
| FCWP7 (24) | VKVGLA*TKAERASRQQRKQRKNRQKT*RRG*TR*KVKGAKAKK |

Example 18

Testing of FCWP 2-7 for Resistance to Proteolysis

Due to the susceptibility of the FCWP1 parent protein to proteolysis, a gel assay was used to evaluate the susceptibility of the mutants to proteolysis. The variants of FCWP1 were subjected to proteolysis by pIWF for 5 minutes under the conditions described previously. The degree of protein degradation was determined by analysis on 16.5% Tricine-SDS polyacrylamide gels (Bio-Rad, Hercules, Calif.) with visualization of the proteins by silver staining (Novex, San Diego, Calif.).

The results indicated that FCWP5, FCWP6, and FCWP7 were more resistant than the other FCWP proteins to proteolysis in potato intercellular wash fluid in vitro. The protease susceptible sites of the variants were further characterized by limited proteolysis and MALDI-TOF mass spectrometry as described previously. This analysis confirmed that FCWP5, FCWP6, and FCWP7 were more resistant to proteolysis.

Example 19

Testing the Antifungal Activity of FCWP 2-7 Proteins

Each of the FCWP proteins was tested in an antifungal activity assay (as described in Example 4). The results are listed in Table 5. All the variant proteins tested possessed antifungal activity against *Phytophthora infestans* at concentrations similar to that of the wild-type protein. The minimum inhibitory concentration was in the range of 10-25 ppm for all proteins. Notably, FCWP7 retained its antifungal activity for 60 hours. By comparison, wild-type FCWP1 has no activity at 60 hours.

In a separate assay, antifungal activity was assessed in the presence of dilute amounts of pIWF (i.e., under conditions of proteolysis). These assays demonstrated that FCWP3, FCWP5, and FCWP7 retained full activity in the presence of pIWF where the wild-type protein is only slightly active.

TABLE 5

Activity and Stability of FCWP Proteins against *P.infestans**

| Protein | IC$_{50}$ (24 hours) | IC$_{50}$ (60 hours) |
|---|---|---|
| FCWP1 | 15 ppm | >100 ppm |
| FCWP2 | 25 ppm | >100 ppm |
| FCWP3** | 25 ppm | >100 ppm |
| FCWP4 | 20 ppm | >100 ppm |
| FCWP5** | 50 ppm | >100 ppm |
| FCWP6 | 25 ppm | >100 ppm |
| FCWP7** | 10 ppm | 25 ppm |

*Concentrations of protein tested were 100 ppm, 50 ppm, 10 ppm, 2 ppm, and 1 ppm.
**These proteins also retained their activity at 50 ppm in the presence of 10 ppm pIWF.

The proteins were also tested in the assay against *Verticillium dahliae*. Stocks of the proteins were prepared in 50 mM HEPES buffer, pH 7.5. A 10 µL suspension of *Verticillium dahliae* conidia was added to 10 µL of protein solution. The spores were allowed to germinate at room temperature for about 4 hours. After germination, the protein was added and the assay incubated at room temperature overnight. Inhibition of fungal growth was determined by microscopic evaluation of the fungal/protein mixture. Again, all the FCWP proteins demonstrated antifungal activity similar to the wild-type protein (Table 6). The proteins were assayed at final concentrations of 25 ppm and 10 ppm and an average inhibitory concentration was determined.

TABLE 6

Activity of FCWP Proteins against *Verticillium dahliae*.

| Protein | IC$_{50}$ (24 hours) |
|---|---|
| FCWP1 | 10 ppm |
| FCWP2 | 20 ppm |
| FCWP3 | 10 ppm |
| FCWP4 | 20 ppm |
| FCWP5 | <10 ppm |
| FCWP6 | 25 ppm |
| FCWP7 | <10 ppm |

Example 20

Construction of Plasmids Containing fcwp2-7

The recombinant vector pMON21454 (constructed in Example 7), was used as a PCR template to produce nucleic acid sequences that encode SEQ ID NOS:19-24 (FCWP2-7, respectively). Primers consisted of a 5' oligomer (SEQ ID NO:7) and a unique oligomer complementary to the 3' end of each of the respective fcwp sequences. Each of these 3' oligomers (SEQ ID NOS: 25-30) was designed to incorporate either a single or double amino acid substitution in the resulting amino acid sequence. Each oligomer was also designed to introduce a BamHI restriction site after the stop codon. In this manner, fcwp2-7 were produced.

PCR products were produced and gel purified as described previously. The purified DNA fragments were digested with BamHI and ligated into plasmid pMON22575 to produce pMON 32682-32687, which correspond to fcwp variants 7, 2, 3, 4, 5, and 6, respectively.

The sense orientation and DNA sequence of each variant was verified and the NotI fragment containing the gene expression cassette was subcloned into a binary vector pMON26140.

Example 21

Identification of Proteins Related to FCWP1

Protein and nucleic acid databases were searched in an attempt to identify sequences related to FCWP1. No sequences were found with significant sequence homology. Proteins falling in the same class of antifungal proteins were identified by searching in the public sequence databases using the search string "ribosom." The software used for searching was the LookUp program supplied with GCG version 9.1 (Genetics Computer Group, Inc., Madison, Wis.). The set of sequences returned was edited by a biologist to eliminate sequences that were not ribosomal proteins. The edited set was then searched using IsoSearch.

The predicted isoelectric point (pI) of each protein was calculated using the HasIsoPoint algorithm in GCG version 9.1 pK data was obtained from the isoelectric.dat table supplied with GCG version 9.1. (Bull, 1964). Protein mass was calculated using the average atomic masses of unhydrated amino acids derived from the aafreq.dat table supplied with GCG version 9.1.

A group of related proteins was discovered that had similar values for pI and molecular weight (SEQ ID NOS: 37-1753). These proteins were ribosomal and typically had a pI greater than 7 and a molecular weight below about 20 kDa. A representative number of proteins from this group were selected and tested for antifungal activity. The assay was performed as described previously. The related proteins displayed significant antifungal activity (Table 7).

TABLE 7

Antifungal Activity of Ribosomal Proteins Related to FCWP1.

| Protein | SEQ ID NO: | # AA | Molecular Weight (Da) | pI | IC$_{50}$ (µM) P. infestans | IC$_{50}$ (µM) F. culmorum |
| --- | --- | --- | --- | --- | --- | --- |
| FCWP1 | 1 | 40 | 4504 | 12.14 | 5 | 5 |
| YL41 | 35 | 25 | 3337 | 12.96 | 4.5 | 1.2 |
| YL46 | 34 | 50 | 6228 | 12.55 | 6.4 | 1.3 |
| SL23 | 33 | 44 | 5192 | 12.13 | 7.7 | 2.5 |
| BL36 | 32 | 37 | 4427 | 12.91 | 3.4 | 2.3 |
| BL32 | 31 | 52 | 6061 | 12.05 | 6.6 | 1.6 |

Example 22

Production of Transformed Plant Cells

The recombinant vectors from Example 20 were used to transform *Agrobacterium tumefaciens* via electroporation. Plasmids pMON32684, pMON32686, pMON32687, and pMON32682 (corresponding to FCWP variants 3, 5, 6, and 7, respectively) were used to generate transgenic potato plants via *Agrobacterium*-mediated transformation of potato plant cells (Fraley et al., 1983).

Example 23

Testing Transgenic Potato Plants for Resistance to *Phytophthora infestans*

Russet Burbank potato plants (*Solanum tuberosum*) producing FCWP proteins will be tested for resistance to fungal infections. Transgenic and non-transgenic plantlets will be propagated from callus (soft tissue that forms over a wounded or cut slant surface). When plantlets reach approximately 1-2 inches tall, the plants will be removed from the medium and transplanted into 6-inch pots containing Metro-Mix 350 (Hummert Seed Co., St. Louis) and placed in a growth chamber. Six pots with three to four shoots each (10 leaves with 5-7 leaves/shoot, 4-5 weeks after transplanting) will be used for each test.

The potato plants will be challenged with an inoculation of *Phytophthora infestans*. The *Phytophthora infestans* sample will preferably be introduced as an infected potato tissue (foliage or stems).

*P. infestans* is typically isolated by placing infected tissue directly underneath fresh potato tuber slices in sterile 9-cm petri plates. Mycelia of *P. infestans* grow through the tuber slices and sporulate within approximately 7-10 days. Sporangia produced by mycelia grow through the tuber slices and are transferred to fresh media on a small agar block. Using this method, a clean culture is obtained without the need for selective media. Long-term culture of the isolate is achieved by maintaining the culture on a medium such as rye A agar medium (Caten and Jinks, 1968)

A preferred *Phytophthora infestans* isolate for use in disease tests would be the most agronomically significant isolate available, which currently is US-8, mating type A2. *Phytophthora* isolates generally are typed by comparison profiles of enzymes electrophoretically using a known Pi strain as a standard.

For inoculation, a *P. infestans* sporangial suspension will be prepared using cold (4° C.) deionized distilled water with approximately $1 \times 10^4$ sporangia per milliliter. The *P. infestans*, for example US-8, will be inoculated onto the leaf surface of the plants with the aid of a spray gun such as a DeVilbiss EGA-502 (Sunrise Medical Co., Somerset, Pa.) or equivalent method. Inoculated plants will then be placed in a moist growth chamber at approximately 17° C. in the dark for approximately 40 hours. Next, the plants will be transferred to a growth chamber for subsequent analysis of fungal disease symptoms. The growth chamber conditions will be approximately 18° C., 12 hr light per day, and about 320 µE per square meter per second.

Disease severity will generally be assessed at two different time points. At 4- and 7-days post-inoculation, the plants will be scored based on the percentage of diseased leaf tissue and compared with appropriate controls.

The plants produced in this fashion may include nucleic acid sequences encoding the wild-type FCWP1, the FCWP 2-7 variants, other modified forms of FCWP1, and other related ribosomal proteins identified on the basis of their high pI and low molecular weight such as SEQ ID NOS: 31-35.

Example 24

Production of a Nucleic Acid Sequences Encoding the BL36 Protein

The BL36 antifungal protein consists of 37 amino acids. Using the amino acid sequence of SEQ ID NO:32, a nucleic acid molecule encoding BL36 was constructed by PCR.

Due to the degeneracy of the genetic code, several codons are possible for any particular amino acid. Each type of cell or organism, however, has a preferred pattern of codon usage. The codon usage was selected such that it was optimal for dicots or monocots. Optimal codon usage was determined as described (Murray et al., 1989) and codon frequency table for potato or maize in Wisconsin GCG software package (Genetics Computer Group, Inc., Madison, Wis.).

The bl36 synthetic gene was fused to a second nucleic acid sequence encoding a signal peptide from the AlfAFP protein. The signal sequence is described in U.S. patent application Ser. No. 09/003,198. Immunohistochemical studies indicated that this signal peptide functions to target the protein to the extracellular space of plant tissue.

Reactions (3' extension of the annealed PCR products and the PCR amplification of the full length sequence) of overlapping oligonucleotides were conducted in a single tube, in a single PCR reaction using the Long Range Template PCR kit (Boehringer Mannheim Corp., Indianapolis, Ind.) following the conditions suggested by the manufacturer to produce full-length synthetic genes (SEQ ID NO:37 for the bl36 potato synthetic gene and SEQ ID NO:36 for the bl36 wheat synthetic gene. The kit included all the necessary enzymes and buffers. Oligonucleotide primers were produced by Midland Certified Reagent Co., (Midland, Tex.). Convenient restriction sites were added to the ends to facilitate subcloning. The final PCR product was separated on a 2% agarose gel, and a nucleic acid band of about 140 base pairs was visualized after ethidium bromide staining. This nucleic acid band was purified from the gel and ligated into plasmid (Invitrogen, San Diego, Calif.).

The sequence of the synthetic gene was confirmed using a 373 DNA Sequencer Stretch Model from Applied Biosystem using the PRISM Ready Reaction Dideoxy Terminator Cycle Sequencing Kit following the manufacturer's instructions (Applied Biosystems, Inc., Foster City, Calif.).

Figure 6:
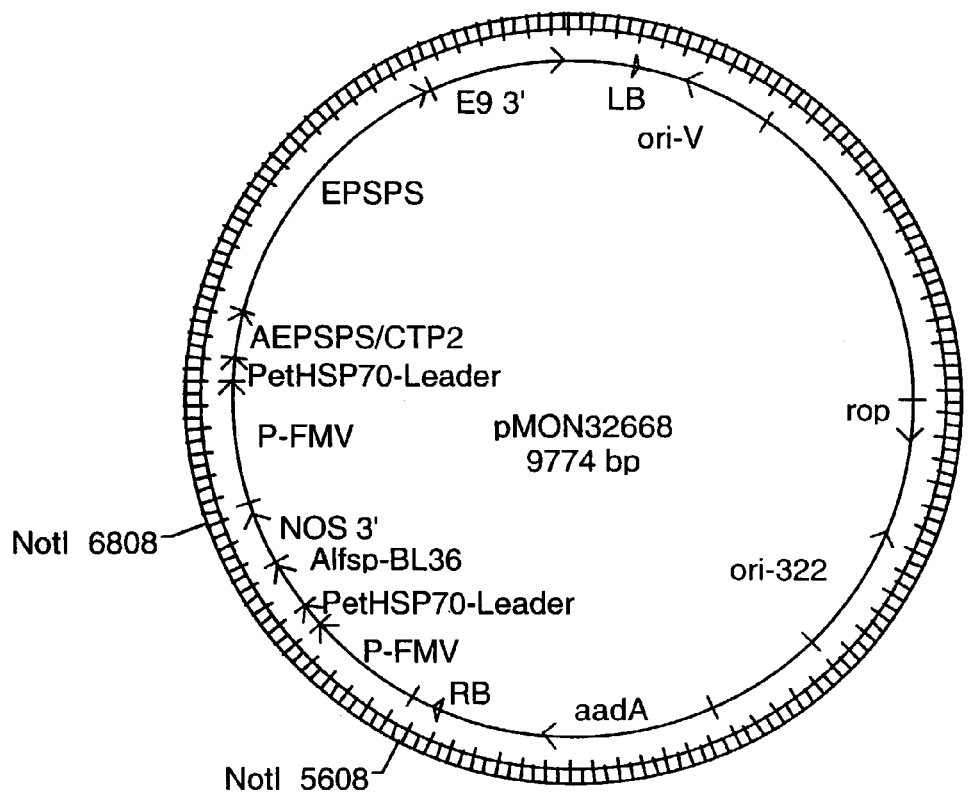
FIG. 6 is a plasmid map of pMON32668.

For the potato gene, Bam HI and EcoR I restriction sites were used to subclone the bl36 gene into pMON22575 for expression behind the FMV promoter, resulting in pMON32658. The expression cassette was transferred as a Not I fragment into the double-border plant transformation vector pMON21460 to produce pMON32668 (FIG. 6). Potato plants were transformed with pMON32668 using the method in Example 22 and tested for disease resistance by the method in Example 23. No disease resistance was seen.

Figure 7:
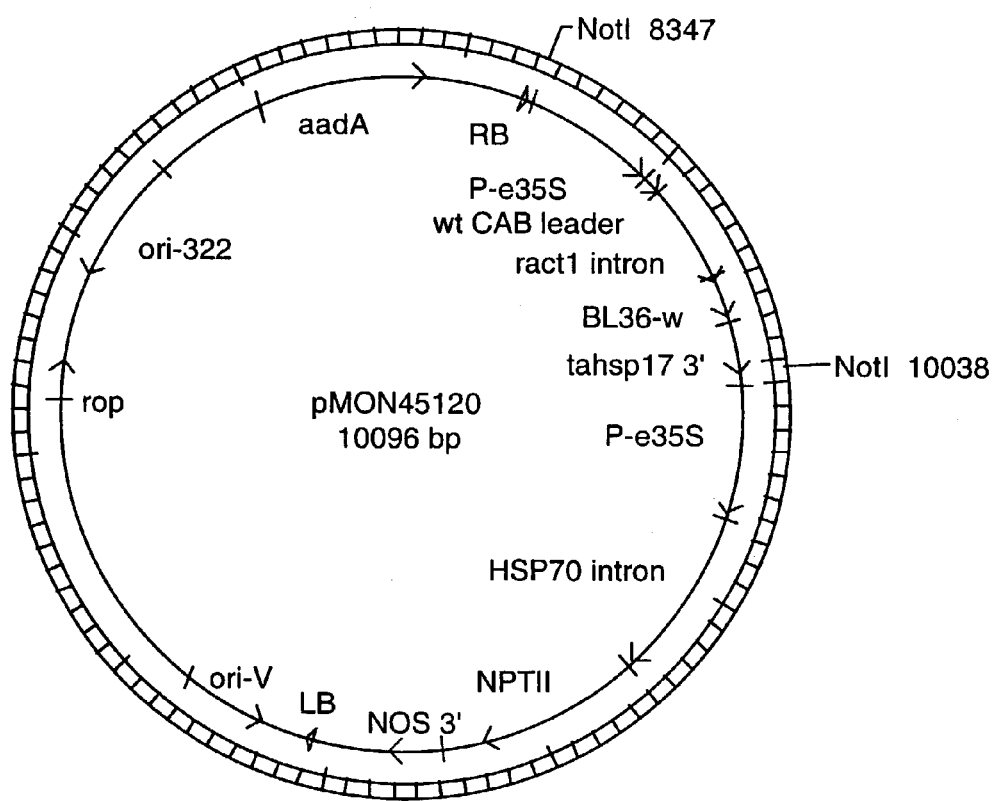
FIG. 7 is a plasmid map of pMON45120.

For the wheat gene, the PCR produced synthetic gene was ligated into pMON32619, behind the e35S promoter at Nco I and Eco RI to produce pMON21465. The Not 1 cassette was mobilized into the double-border plant transformation vector pMON36147 to produce pMON45120 (FIG. 7).

Transformation of Wheat

For transformation of wheat plants, pMON45120 was used and the following procedure was followed.

1. Explant Preparation

Immature embryos of wheat (*Triticum aestivum* L) cv Bobwhite were isolated from the immature caryopsis (wheat spikelets) 13-15 days after pollination, and cultured on CM4C (Table 8) for 3-4 days. The embryos without embryogenic callus were selected for *Agrobacterium* inoculation.

TABLE 8

Supplemental Components in Basal Media[1]

| Components | CM4 | CM4C | MMS.2C | MMS0 |
|---|---|---|---|---|
| 2,4-D (mg/L) | 0.5 | 0.5 | 0.2 | — |
| Pichloram (mg/L)[2] | 2.2 | 2.2 | | |
| Maltose (g/L) | 40.0 | 40.0 | 40.0 | 40.0 |
| Glutamine (g/L) | 0.5 | 0.5 | | |
| Magnesium Chloride (g/L) | 0.75 | 0.7 | | |
| Casein Hydrolysate (g/L) | | 0.1 | 0.1 | |
| MES (g/L) | | 1.95 | 1.95 | 1.95 |
| Ascorbic Acid (mg/L)[2] | 100.0 | 100.0 | 100.0 | |
| Gelling Agent (g/L)[3] | 2(P) | 2(P) | 2(G) | 2(G) |

[1]All media contain basal salts (MS basal salts) and vitamins (MS vitamins) from Murashige and Skoog (1962). The pH in each medium was adjusted to 5.8.
[2]Filter-sterilized and added to the medium after autoclaving.

[3]PHYTAGEL (P) (PHYTAGEL is a registered trademark of Sigma Chemical Co., St. Louis, Mo.) or GELRITE (G) (GELRITE is available from Schweizerhall, Inc., South Plainfield N.J.) (GELRITE is a registered trademark of Monsanto Company, St. Louis, Mo.).

2. *Agrobacterium* Culture and Inoculation

A disarmed *Agrobacterium* strain C58 (ABI) harboring a binary vector was used for all the experiments. Cultures of *Agrobacterium* were initiated from glycerol stocks or from a freshly streaked plate and grown overnight at 26° C.-28° C. with shaking (approximately 150 rpm) to mid-log phase (about $OD_{660}$=1-1.5) in liquid LB medium, pH 7.0 (Miller, 1972) containing 50 mg/L kanamycin, 50 mg/L streptomycin and spectinomycin, and 25 mg/L chloramphenicol with 200 µM acetosyringone (AS). The *Agrobacterium* cells were resuspended in the inoculation medium and the density was adjusted to an $OD_{660}$ of 1. The immature embryos cultured in CM4C medium were transferred into sterile petri plates (16×20 mm) or wells of a 6-well cell culture plate (Costar Corporation, Cambridge, Mass.) containing 10 mL of inoculation medium per petri plate or 5 mL per cell culture cluster plate. An equal amount of the *Agrobacterium* cell suspension was added such that the final concentration of *Agrobacterium* cells was an $OD_{600}$ of 0.5 or in some experiments 0.25. In most experiments, pluronic F68 was added to the inoculation mixture at a final concentration of 0.01%. The ratio between the *Agrobacterium* and immature embryos (IEs) was about 10 mL: 20-200 IEs. The conditions for inoculation were temperatures from 23° C.-26° C. with a duration from 25-30 minutes.

3. Co-Culture

After the inoculation period, the remaining *Agrobacterium* cells were removed from the explants by using the in-house vacuum equipment. A piece of sterile Whatman No. 1 filter paper (to fit the size of the petri plate) was placed in each of 60×15 or 60×20 mm petri dishes. One hundred and seventy-five to one hundred and ninety microliters of sterile water was placed in the middle of the filter paper. After 2-3 minutes, the inoculated immature embryos were placed in the plates. Usually, 20-50 explants are grouped as one stack (about 1 cm in size and 60-80 mg/stack), with 4-5 stacks on each plate. The plates were immediately parafilmed and then co-cultivated in the dark at 24° C.-26° C. for 2-3 days.

4. Selection and Regeneration

After 2-3 days on the delay medium, the immature embryos were transferred to CM4C supplemented with 25 mg/L G418 and 500 mg/L carbenicillin. After 2-3 weeks, the embryos were broken into smaller pieces (~2 mm) and subcultured to the first regeneration medium, MMS.2C (Table 8) with 25 mg/L G418 and 250 mg/L carbenicillin. Upon transfer to the regeneration medium, each piece of callus was further divided into several small pieces (~2 mm). Two weeks post-transfer, young shoots and viable callus tissue were transferred to a second regeneration medium MMS0C (Table 8) with the same concentrations of G418 and carbenicillin. Larger pieces of tissues were separated into smaller pieces as previously described. Plantlets, which were confirmed later to be true transformants, grew vigorously and formed strong root systems on this medium. The plants with strong root hairs, with more than ten short and strong roots, or secondary roots, were transferred to Sundae cups (Sweetheart Cup Company, Chicago, Ill.) containing the second regeneration medium for further growth and selection. During the growth period in the Sundae cups, most of the non-transformants died or showed signs of susceptibility to G418. The plants highly resistant to G418, which grew vigorously with strong root systems, were transferred to soil before they grew to the top of the Sundae cups. All the plants that originated from the same embryo were considered to be siblings from the same event.

5. Detection and Analysis of the Transgenic Plants

The plants were grown in an environmentally controlled growth chamber with a 16-hour photoperiod at 800 molm$^{-2}$s$^{-1}$ provided by high-intensity discharge (HID) Sylvania lights (GTE Products Corp., Manchester, N.H.). The day/night temperatures were 18/16° C. It took about 2.5 to 3 months from inoculation to transferring most of the plants to soil, and no visible abnormalities were observed. Each plant is tested for disease activity as described below.

Two experiments were conducted to evaluate the activity of BL36 using e35S promoter (pMON45120) in wheat to control *Fusarium* head blight (*Fusarium graminearum*) and Glume Blotch (*Stagonospora nodorum*) in the growth chamber.

In these experiments a total of 37 BL36 transgenic lines were submitted for the *Fusarium* head blight (*F. graminearun*) and Glume Blotch (*S. nodorum*) disease testing. Both experiments were arranged in a randomized complete block design, replicated 5 times for each disease. For comparison, in both experiments, 37 BL36 negative lines and 37 non-transgenic susceptible Bobwhite plants were included to benchmark the efficacy of the BL36 positive transgenic lines.

In the *Fusarium* head blight (*F. graminearum*) experiment, transgenic wheat lines have been assayed using the point inoculation technique. Wheat heads were inoculated with a mycelial plug of *F. graminearum* when the flowers were in the process of anthesis or when the head already extruded anthers. The first disease evaluation was performed 5 days after inoculation by counting the number of spikelets that exhibited disease symptoms. Evaluations were repeated at 2 day intervals for a total of 6 times. Disease severity was expressed as the percentage of diseased spikelets per spike for each time point. To test the overall treatment effect, the area under disease progress curve (AUDPC) was calculated for each transgenic plant. In this experiment, six of the 37 lines had a lower AUDPC than the controls.

In the Glume Blotch (*Stagonospora nodorum*) experiment, conidial suspension of *S. nodorum* used for inoculation was adjusted to 2×106 spores per milliliter. Inoculated plants were then placed in a mist chamber for 78 hours before moved to the growth chamber. Plants were rated at 7 and 14 days after inoculation. In this experiment, each plant was visually assessed and rated as the mean percent glume diseased on a scale 0-100%. The average percent disease for the negative plants was 63%. Twenty-four of the 37 BL36 plants had a lower percent disease, with the lowest being 45%.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

REFERENCES

Ainley et al., *Plant Mol. Biol.* 14: 949, 1990
Ausubel et al., *Current Protocols in Molecular Biology*, John Wiley and Sons, Inc., 1995.
Back et al., *Plant Mol. Biol.* 17: 9, 1991
Bauer et al., *Gene*, 37: 73, 1985.
Bol et al., *Ann. Rev. Phytophathol*, 28: 13-138, 1990.
Bowles, *Ann. Rev. Biochem*, 59: 873-907, 1990.
Brears et al., *Agro-Food-Industry Hi-Tech.*, 10-13, 1994.
Broekaert et al., *Plant Physiol.*, 108:1353-1358, 1995.
Broekaert et al., *Critical Reviews in Plant Sciences*, 16(3): 297-323, 1997.
Bull, *An Introduction to Physical Biochemistry*, Philadelphia, F. A. Davis, Co, p. 128, 1964.
Bustos et al., *EMBO J.* 10: 1469-1479, 1991.
Campbell et al., *Plant Physiol.*, 92: 1-11, 1990.
Capecchi, *Cell*, 22(2): 479-488, 1980.
Castresana et al., *EMBO J.* 7: 1929-1936, 1988
Caten and Jinks, *Canadian Journal of Botany*, 46: 329, 1968.
Celano et al., *Biotechniques*, 1:26-28, 1993.
Cerda-Olmedo et al., *J. Mol. Biol.* 33: 705-719, 1968
Chau et al., *Science*, 244:174-181. 1989.
Christensen et al., *Plant Mol. Biol.*, 18: 675, 689, 1992.
Clapp, *Clin. Perinatol.*, 20(1): 155-168, 1993.
Costa et al., *Methods Mol. Biol.* 57: 31-44, 1996
Craik, *BioTechniques*, 3: 12-19, 1985.
Curiel et al., *Hum. Gen. Ther.*, 3(2):147-154, 1992.
Cuypers et al, *Mol. Plant-Microbe Interact*, 1: 157-160, 1988.
Davey et al., *Symp. Soc. Exp. Biol.* 40: 85-120, 1986.
Davey et al., *Plant Mol. Biol.* 13(3): 273-285, 1989.
Deng and Nickloff, *Anal. Biochem.* 200: 81, 1992
Doyle et al., *J. Biol. Chem.* 261: 9228-9238, 1986
Eglitis and Anderson, *Biotechniques*, 6(7): 608-614, 1988.
Feinbaum et al., *Mol. Gen. Genet.* 226: 449-456, 1991
Fraley et al., *Proc. Natl. Acad. Sci. U.S.A.*, 80: 4803, 1983.
Frits Eckstein et al., *Nucleic Acids Research*, 10: 6487-6497, 1982.
Fritzemeier et al., *Plant Physiol.*, 85: 34-41, 1987.
Fromm et al., *Proc. Natl. Acad. Sci. USA*, 82(17): 5824-5828, 1985.
Fynan et al., *Proc. Natl. Acad. Sci. USA*, 90(24): 11478-11482, 1993.
Gasser and Fraley, *Science* 244: 1293, 1989.
Glick et al., Methods in Plant Molecular Biology and Biotechnology, CRC Press, Boca Raton, Fla., 1993.
Graham and Van der Eb, *Virology*, 54(2): 536-539, 1973.
Greener et al., *Mol. Biotechnol.* 7: 189-195, 1997
Guerola et al., *Nature New Biol.* 230: 122-125, 1971
Hershey and Stoner, *Plant Mol. Biol.* 17: 679-690, 1991
Hess, *Intern Rev. Cytol.*, 107: 367, 1987.
Horsch et al., *Science*, 227: 1229-1231, 1985.
Johnston and Tang, *Methods Cell Biol.*, 43(A): 353-365, 1994.
Kares et al., *Plant Mol. Biol.* 15: 905, 1990
Keller et al., *EMBO L.*, 8: 1309-1314, 1989.
Knutzon et al., *Proc. Natl. Acad. Sci. U.S.A.* 89: 2624-2628, 1992
Kridl et al., *Seed Sci. Res.* 1: 209, 1991
Kuhlemeier et al., *Plant Cell* 1: 471, 1989
Kunkel, *Proc. Natl. Acad. Sci. U.S.A.*, 82: 488-492, 1985
Kyte and Doolittle, *J. Mol. Biol.*, 157: 105-132, 1982
Lam and Chua, *J. Biol. Chem.* 266: 17131-17135, 1990

Lam and Chua, *Science* 248: 471, 1991
Laemmli, *Nature,* 227: 680-685, 1970.
Lindstrom et al., *Developmental Genetics,* 11: 160, 1990.
Linthorst, *Crit. Rev. Plant Sci.,* 10: 123-150, 1991.
Logemann et al., *Plant Cell,* 1: 151-158, 1989.
Lu et al., *J. Exp. Med.,* 178(6): 2089-2096, 1993.
Luo et al., *Plant Mol. Biol. Reporter,* 6: 165, 1988.
Mandel et al., *Plant Mol. Biol,* 29: 995-1004, 1995.
Martens K., *Spray Drying Handbook,* Third Edition, G. Goodwin, Ltd., London, 1979.
Martini et al., *Mol. Gen. Genet.,* 263: 179, 1993.
Matton et al., *Mol. Plant-Microbe Interact,* 2: 325-331, 1989.
McElroy et al., *Plant Cell,* 2:163-171, 1990.
Murray et al., *Nucl. Acids Res.,* 17(2):477-498, 1989.
Neuhaus et al., *Theor. Appl. Genet.,* 75: 30, 1987.
Odell et al., *Nature,* 313: 810, 1985.
Osuna et al., *Critical Reviews In Microbiology,* 20: 107-116, 1994.
Ou-Lee et al., *Proc. Natl. Acad. Sci. U.S.A.* 83: 6815, 1986
Park et al., *Plant Molecular Biology,* 32(6): 1135-1148, 1996.
Pena et al., *Nature,* 325: 274, 1987.
Poszkowski et al., *EMBO J.,* 3: 2719, 1989.
Potrykus, et al., *Ann. Rev. Plant Physiol. Plant Mol. Biol.,* 42: 205, 1991.
Pyee et al., *Plant J.,* 7: 49-59, 1995.
Richins et al., *Nucleic Acids Res.* 20: 8451, 1987
Rodriguez, et al. Vectors: A Survey of Molecular Cloning Vectors and Their Uses, Butterworths, Boston, 1988.
Rogan and Bessman, *J. Bacteriol.* 103: 622-633, 1970
Rogers et al., *Meth. In Enzymol,* 153: 253-277, 1987.
Samac et al., *Plant Cell,* 3:1063-1072, 1991.
Sambrook et al., *Molecular Cloning: A Laboratory Manual,* Second Edition, Cold Spring Harbor Laboratory Press, Cold Spring Harbor, N.Y., 1989.
Schroder et al., *Plant J.,* 2: 161-172, 1992.
Schulze-Lefert et al., *EMBO J.* 8: 651, 1989
Simpson, *Science,* 233: 34, 1986.
Singer and Kusmierek, *Ann. Rev. Biochem.* 52: 655-693, 1982
Slighton and Beachy, *Planta* 172: 356, 1987
Smith et al, In: *Genetic Engineering: Principles and Methods,* Setlow et al., Eds., Plenum Press, N.Y., 1-32, 1981.
Sosa et al., *Nucleic Acids Res.,* 17(22): 9319-9331, 1989.
Stayton et al., *Aust. J. Plant. Physiol.* 18: 507, 1991
Terras et al., *J. Biol. Chem.,* 267: 15301-15309, 1992.
Terras et al., *FEBS Letters,* 316(3): 233-240, 1993.
Vandeyar et al., *Gene* 65: 129-133, 1988
Van Tunen et al., *EMBO J.* 7: 1257, 1988.
Vodkin et al., *Cell,* 34: 1023, 1983.
Vogel, et al., *J. Cell Biochem.,* (Suppl) 13D: 312, 1989.
Wagner et al., *Proc. Natl. Acad. Sci. USA,* 89(13): 6099-6103, 1992.
Walder et al., *Gene,* 42: 133, 1986.
Watkins, *Handbook of Insecticide Dust Diluents and Carriers,* Second Edition, Darland Books, Caldwell, N.J.
Weissbach and Weissbach, *Methods for Plant Molecular Biology,* (Eds.), Academic Press, Inc., San Diego, Calif., 1988.
Weisshaar et al., *EMBO J.* 10: 1777-1786, 1991
Wenzler et al., *Plant Mol. Biol.,* 12: 41-50, 1989.
Williams et al., *Biotechnology* 10: 540-543, 1992
Winnacker-Kuchler, *Chemical Technology,* Fourth Edition, Volume 7, Hanser Verlag, Munich, 1986.
Wong and Neumann, *Biochim. Biophys. Res. Commun.,* 107(2): 584-587, 1982.
Worthington and Walker, *The Pesticide Manual,* Seventh Edition, British Crop Protection Council, 1983.
Yamaguchi-Shinozaki et al., *Plant Mol. Biol.* 15: 905, 1990.
Yang and Russell, *Proc. Natl. Acad. Sci. USA,* 87:4144-4148, 1990.
Zatloukal et al., *Ann. N.Y. Acad. Sci.,* 660: 136-153, 1992.
Zhou et al., *Methods in Enzymology,* 101: 433, 1983.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07332596B1). An electronic copy of the "Sequence Listing" will also be available from the USPTO upon request and payment of the fee set forth in 37 CFR 1.19(b)(3).

---

What is claimed is:

1. An isolated nucleic acid segment comprising SEQ ID NO:2, wherein said nucleic acid segment encodes an antifungal protein.

2. The isolated nucleic acid segment of claim 1, wherein said antifungal protein is SEQ ID NO:1.

3. The isolated nucleic acid segment of claim 1, wherein said segment is a plant, fungal, or bacterial nucleic acid sequence.

4. A recombinant vector comprising operatively linked in the 5' to 3' direction:

a promoter which functions in a plant cell;

a structural nucleic acid sequence having at least 95% or about 95% sequence identity to SEQ ID NO:2, wherein said nucleic acid sequence encodes an antifungal protein;

a 3' transcriptional termination signal; and a 3' polyadenylation signal.

5. The recombinant vector of claim 4, wherein the promoter is selected from the group consisting of the nopaline synthase (NOS) promoter, octopine synthase (OCS) promoter, mannopine synthase (mas) promoter, cauliflower mosaic virus 19S and 35S (CaMV19S, CaMV35S) promoter, enhanced CaMV (eCaMV) promoter, ribulose 1,5-bisphosphate carboxylase (ssRUBISCO) promoter, figwort mosaic virus (FMV) promoter, CaMV derived AS4 promoter, tobacco RB7 promoter, wheat POX1 promoter, tobacco EIF-4 promoter, lectin protein (Le1) promoter, and rice RC2 promoter.

6. A transformed host cell comprising operatively linked in the 5' to 3' direction:
   a promoter which functions in a plant cell;
   a structural nucleic acid sequence having at least 95% or about 95% sequence identity to SEQ ID NO:2, wherein said nucleic acid sequence encodes an antifungal protein;
   a 3' transcriptional termination signal; and
   a 3' polyadenylation signal.

7. The transformed host cell of claim 6, wherein the structural nucleic acid sequence encodes a protein having at least 95% or about 95% sequence identity to SEQ ID NO:1.

8. The transformed host cell of claim 6, wherein the structural nucleic acid sequence encodes SEQ ID NO:1.

9. The transformed host cell of claim 6, wherein the structural nucleic acid sequence is at least 95% identical to SEQ ID NO:2 and encodes an amino acid sequence variant of SEQ ID NO:1 selected from the group consisting of SEQ ID NO:19, SEQ ID NO:20, SEQ ID NO:21, SEQ ID NO:22, SEQ ID NO:23, and SEQ ID NO:24.

10. The transformed host cell of claim 6, wherein the promoter is seed selective, tissue selective, constitutive, or inducible.

11. The transformed host cell of claim 6, wherein the promoter is selected from the group consisting of the nopaline synthase (NOS) promoter, octopine synthase (OCS) promoter, mannopine synthase (mas) promoter, cauliflower mosaic virus 19S and 35S (CaMV19S, CaMV35S) promoter, enhanced CaMV (eCaMV) promoter, ribulose 1,5-bisphosphate carboxylase (ssRUBISCO) promoter, figwort mosaic virus (FMV) promoter, CaMV derived AS4 promoter, tobacco RB7 promoter, wheat POX1 promoter, tobacco EIF-4 promoter, lectin protein (Le1) promoter, and rice RC2 promoter.

12. The transformed host cell of claim 6, wherein the structural nucleic acid sequence is a synthetic plant, fungal, or bacterial structural nucleic acid sequence.

13. The transformed host cell of claim 12, wherein the transformed host cell is a prokaryotic cell.

14. The transformed host cell of claim 13, wherein the transformed host cell is an *Escherichia coli* cell.

15. The transformed host cell of claim 12, wherein the transformed host cell is a eukaryotic cell.

16. The transformed host cell of claim 15, wherein the transformed host cell is a fungal cell.

17. The transformed host cell of claim 15, wherein the transformed host cell is a plant cell.

18. The transformed host cell of claim 17, wherein the transformed host cell is an alfalfa, apple, banana, barley, bean, broccoli, cabbage, carrot, castorbean, celery, citrus, clover, coconut, coffee, corn, cotton, cucumber, garlic, grape, linseed, melon, oat, olive, onion, palm, parsnip, pea, peanut, pepper, potato, radish, rapeseed, rice, rye, sorghum, soybean, spinach, strawberry, sugarbeet, sugarcane, sunflower, tobacco, tomato, or wheat cell.

19. The transformed host cell of claim 17, wherein a transgenic plant is regenerated from said host cell.

20. The transformed host cell of claim 19, wherein said transgenic plant is an *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplants endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palms papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yam, or zucchini plant.

\* \* \* \* \*